United States Patent
Heine et al.

(10) Patent No.: US 9,304,973 B2
(45) Date of Patent: Apr. 5, 2016

(54) METHOD FOR ASSESSING BREAST DENSITY

(75) Inventors: John J. Heine, New Port Richey, FL (US); Thomas A. Sellers, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 152 days.

(21) Appl. No.: 13/994,969

(22) PCT Filed: Dec. 15, 2011

(86) PCT No.: PCT/US2011/065091
§ 371 (c)(1),
(2), (4) Date: Jun. 17, 2013

(87) PCT Pub. No.: WO2012/082994
PCT Pub. Date: Jun. 21, 2012

(65) Prior Publication Data
US 2013/0272595 A1    Oct. 17, 2013

Related U.S. Application Data

(60) Provisional application No. 61/423,390, filed on Dec. 15, 2010.

(51) Int. Cl.
*G06K 9/00* (2006.01)
*G06F 17/18* (2006.01)
(Continued)

(52) U.S. Cl.
CPC .............. *G06F 17/18* (2013.01); *A61B 5/4312* (2013.01); *A61B 6/502* (2013.01); *A61B 6/5217* (2013.01); *A61B 6/583* (2013.01); *G06F 19/345* (2013.01); *G06F 19/3431* (2013.01);
(Continued)

(58) Field of Classification Search
CPC ..................... G06T 2207/30068; G06K 9/623; G06K 9/00496
See application file for complete search history.

(56) References Cited

U.S. PATENT DOCUMENTS 6,282,305 B1 * 8/2001 Huo et al. ..................... 382/128
6,654,445 B2 * 11/2003 Shepherd et al. ............... 378/53
(Continued)

OTHER PUBLICATIONS

"A calibration approach to glandular tissue composition estimation in digital mammography", J. Kaufhold, J. A. Thomas, J. W. Eberhard, C. E. Galbo, and D. E. González Trotter, Medical Physics 29, 1867 (2002).*
(Continued)

*Primary Examiner* — Utpal Shah
(74) *Attorney, Agent, or Firm* — Meunier Carlin & Curfman LLC

(57) ABSTRACT

Breast density is a significant breast cancer risk factor measured from mammograms. Evidence suggests that the spatial variation in mammograms may also be associated with risk. The variation in calibrated mammograms as a breast cancer risk factor was investigated and its relationship with other measures of breast density was explored using full field digital mammography (FFDM) as described herein. A matched case-control analysis was used to assess a spatial variation breast density measure in calibrated FFDM images, normalized for the image acquisition technique variation. The findings indicate the variation measure is a viable automated method for assessing breast density. Insights gained by this work may be used to develop a standard for measuring breast density.

21 Claims, 18 Drawing Sheets

(51) Int. Cl.
  G06K 9/62    (2006.01)
  A61B 5/00    (2006.01)
  G06F 19/00   (2011.01)
  A61B 6/00    (2006.01)
  G06T 7/00    (2006.01)

(52) U.S. Cl.
  CPC ........... *G06K 9/00496* (2013.01); *G06K 9/623* (2013.01); *G06T 7/0012* (2013.01); *G06T 2207/10116* (2013.01); *G06T 2207/20076* (2013.01); *G06T 2207/30068* (2013.01)

(56) References Cited

U.S. PATENT DOCUMENTS

| | | | |
|---|---|---|---|
| 2001/0043729 | A1 | 11/2001 | Giger et al. |
| 2003/0174873 | A1* | 9/2003 | Giger et al. .................. 382/128 |
| 2006/0120608 | A1* | 6/2006 | Luo et al. ..................... 382/224 |
| 2007/0025503 | A1 | 2/2007 | Hemmendorff |
| 2008/0159613 | A1 | 7/2008 | Luo et al. |
| 2009/0214096 | A1* | 8/2009 | Andrushkiw et al. ........ 382/131 |
| 2009/0324049 | A1* | 12/2009 | Kontos et al. ................ 382/132 |
| 2010/0124364 | A1* | 5/2010 | Huo et al. ..................... 382/128 |
| 2011/0206261 | A1* | 8/2011 | Huo et al. ..................... 382/132 |
| 2012/0189175 | A1* | 7/2012 | Highnam et al. ............. 382/128 |

OTHER PUBLICATIONS

Heine, John J. et al. "An Automated Approach for Estimation of Breast Density." Cancer epidemiology, biomarkers & prevention : a publication of the American Association for Cancer Research, cosponsored by the American Society of Preventive Oncology 17.11 (2008): 3090-3097.*

Byng, Jeffrey W., et al. "Automated analysis of mammographic densities and breast carcinoma risk." Cancer 80.1 (1997): 66-74.*

Boyd, N., et al., "Mammographic breast density as an intermediate phenotype for breast cancer," The Lancet Oncology, vol. 6, Issue 10, 2005, pp. 798-808.

Boyd, N., et al., "Mammographic density and breast cancer risk: current understanding and future prospects," Breast Cancer Research, vol. 13, No. 223, 2011, 12 pages.

Boyd, N., et al., "Mammographic Density and Breast Cancer Risk: Evaluation of a Novel Method of Measuring Breast Tissue Volumes," Cancer Epidemiology Biomarkers & Prevention, vol. 18, Issue 6, 2009, pp. 1754-1762.

Boyd, N., et al., "Mammographic Density and the Risk and Detection of Breast Cancer," The New England Journal of Medicine, vol. 356, No. 3, 2007, pp. 227-236.

Boyd, N., et al., "Quantitative Classification of Mammographic Densities and Breast Cancer Risk: Results From the Canadian National Breast Screening Study," Journal of the National Cancer Institute, vol. 87, No. 9, 1995, pp. 670-675.

Byng, J.W., et al., "The quantitative analysis of mammographic densities," Phys. Med. Biol., vol. 39, No. 10, 1994, pp. 1629-1638.

Ding, J., et al., "Evaluating the Effectiveness of Using Standard Mammogram Form to Predict Breast Cancer Risk: Case-Control Study," Cancer Epidemiology Biomarkers & Prevention, vol. 17, 2008, pp. 1074-1081.

Harvey, J. et al., "Quantitative Assessment of Mammographic Breast Density: Relationship with Breast Cancer Risk," Radiology, vol. 230, No. 1, 2004, pp. 29-41.

Heine, J.J., et al., "A quantitative description of the percentage of breast density measurement using full-field digital mammography," Acad Radiol., vol. 18, No. 5, May 2011, pp. 556-564.

Heine, J.J., et al., "Calibrated Measures for Breast Density Estimation," Academic Radiology, vol. 18, No. 5, May 2011, pp. 547-555.

Heine, J.J., et al., "Comparing Two Breast Density Metrics for Risk Assessment," Digital Mammography, 2003, pp. 544-546.

Heine, J.J., et al., "Cumulative Sum Quality Control for Calibrated Breast Density Measurements," Medical Physics, vol. 36, Dec. 2009, pp. 5380-5390.

Heine, J.J., et al., "Effective radiation attenuation calibration for breast density: compression thickness influences and correction," BioMedical Engineering Online, vol. 9, 2010, p. 73.

Heine, J.J., et al., "Effective x-ray attenuation coefficient measurements from two full field digital mammography systems for data calibration applications," Biomedical Engineering Online, vol. 7, Mar. 28, 2008, p. 13.

Heine, J.J., et al., "Effective x-ray attenuation measurements with full field digital mammography," Medical Physics., vol. 33, No. 11, Nov. 2006, pp. 4350-4366.

Heine, J.J., et al., "Mammographic Tissue, Breast Cancer Risk, Serial Image Analysis, and Digital Mammography. Part 1. Tissue and Related Risk Factors," Academic Radiology, vol. 9, No. 3, 2002, pp. 298-316.

Heine, J.J., et al., "Mammographic Tissue, Breast Cancer Risk, Serial Image Analysis, and Digital Mammography. Part 2. Serial Breast Tissue Change and Related Temporal Influences," Academic Radiology, vol. 9, No. 3, 2002, pp. 317-335.

Heine, J.J., et al., "On the statistical nature of mammograms," Medical Physics, vol. 26, No. 11, 1999, pp. 2254-2265.

Heine, J.J., et al., "Spectral analysis of full field digital mammography data," Medical Physics, vol. 29, No. 5, 2002, pp. 647-661.

Highnam, R.P., et al., "Mammographic image analysis," European Journal of Radiology, vol. 24, Issue 1, 1997, pp. 20-32.

Mahesh, M., AAPM/RSNA Physics Tutorial for Residents, Digital Mammography: An Overview, RadioGraphics, vol. 24, No. 6, 2004, pp. 1747-1760.

Malkov, S, et al., "Single x-ray absorptiometry method for the quantitative mammographic measure of fibroglandular tissue volume," Medical Physics, vol. 36, No. 12, 2009, pp. 5525-5536.

Manduca, A., et al., "Texture Features from Mammographic Images and Risk of Breast Cancer," Cancer Epidemiology Biomarkers & Prevention, vol. 18, No. 3, Mar. 2009, pp. 837-845.

McCormack, V., et al., "Breast Density and Parenchymal Patterns as Markers of Breast Cancer Risk: A Meta-analysis," Cancer Epidemiology Biomarkers & Prevention, vol. 15, No. 6, 2006, pp. 1159-1169.

Pawluczyk, O., et al., "A volumetric method for estimation of breast density on digitized screen-film mammograms," Medical Physics, vol. 30, No. 3, 2003, pp. 352-364.

Scutt, D., et al., "Breast asymmetry and predisposition to breast cancer," Breast Cancer Research, vol. 8, No. 2, R14, 2006, 7 pages.

Vachon, C., et al., "Mammographic Breast Density as a General Marker of Breast Cancer Risk," Cancer Epidemiology Biomarkers & Prevention, vol. 16, No. 1, 2007, pp. 43-49.

van Engeland, S., et al., "Volumetric Breast Density Estimation From Full-Field Digital Mammograms," IEEE Transactions on Medical Imaging, vol. 25, No. 3, 2006, pp. 273-282.

Vedantham, S., et al., "Full breast digital mammography with an amorphous silicon-based flat panel detector: Physical characteristics of a clinical prototype," Medical Physics, vol. 27, No. 3, 2000, pp. 558-567.

Wolfe, J., "Breast Patterns as an Index for Developing Breast Cancer," American Journal Roentgenology, vol. 126, 1976, pp. 1130-1137.

Wolfe, J., "Risk for Breast Cancer Development Determined by Mammographic Parenchymal Pattern," Cancer, vol. 37, No. 5, 1976, pp. 2486-2492.

Yaffe, M., "Measurement of mammographic density," Breast Cancer Research, vol. 10, No. 3, 2008, p. 209.

International Preliminary Report on Patentability and Written Opinion, dated Jun. 18, 2013, in corresponding International Application No. PCT/US2011/065091.

International Search Report, dated Jul. 20, 2012, in corresponding International Application No. PCT/US2011/065091.

* cited by examiner

| Characteristic | Case, n | Case mean / SD or % | Control, n | Control mean / SD or % |
|---|---|---|---|---|
| Age | 123 | 59.4 / 9.7 | 123 | 59.2 / 9.6 |
| HRT | | | | |
| Never-used | 62 | 50.4% | 68 | 55.3% |
| 1-5 yrs | 24(4) | 19.5% | 21(4) | 17.1% |
| 6-10 yrs | 15(5) | 12.2% | 15(5) | 12.1% |
| 11-15 yrs | 9(5) | 7.3% | 7(4) | 5.7% |
| > 15 yrs | 13(7) | 10.6% | 12(8) | 9.8% |
| BMI (kg/m$^2$) | 123 | 27.1 / 5.1 | 123 | 25.7 / 4.7 |
| Breast area (pixel) | 123 | 1548303 / 69476 | 123 | 1310576 / 443321 |

*FIG. 2*

| Breast density measure | Cancer Side OR (95% CI) | Case | Az | *Non-cancer Side OR (95% CI) | Case | Az |
|---|---|---|---|---|---|---|
| PD | | | | | | |
| BMI adjusted | | | 0.623 | | | 0.647 |
| 1 | 1.00 (Ref.) | 23 | | 1.00 (Ref.) | 17 | |
| 2 | 2.16 (0.91 - 5.15) | 35 | | 2.74 (1.18 - 6.37) | 35 | |
| 3 | 3.25 (1.41 - 7.53) | 30 | | 3.12 (1.20 - 8.08) | 33 | |
| 4 | 2.85 (1.18 - 6.91) | 35 | | 4.88 (1.66 - 14.36) | 36 | |
| BMI, area adjusted | | | 0.693 | | | 0.676 |
| 1 | 1.00 (Ref.) | 23 | | 1.00 (Ref.) | 17 | |
| 2 | 2.33 (0.93 - 5.84) | 35 | | 2.39 (0.99 - 5.73) | 35 | |
| 3 | 5.55 (2.12 - 14.49) | 30 | | 3.65 (1.35 - 9.87) | 33 | |
| 4 | 6.52 (2.19 - 19.39) | 35 | | 6.48 (2.09 - 20.09) | 36 | |
| $PG_{sd}$ | | | | | | |
| BMI adjusted | | | 0.616 | | | 0.651 |
| 1 | 1.00 (Ref.) | 18 | | 1.00 (Ref.) | 19 | |
| 2 | 1.97 (0.93 - 4.25) | 33 | | 3.41 (1.41 - 8.24) | 38 | |
| 3 | 1.73 (0.76 - 3.94) | 29 | | 2.56 (1.02 - 6.43) | 29 | |
| 4 | 3.03 (1.30 - 7.06) | 43 | | 4.78 (1.68 - 13.59) | 35 | |
| BMI, area adjusted | | | 0.696 | | | 0.691 |
| 1 | 1.00 (Ref.) | 18 | | 1.00 (Ref.) | 19 | |
| 2 | 3.48 (1.40 - 8.66) | 33 | | 4.75 (1.84 - 12.26) | 38 | |
| 3 | 6.25 (2.04 - 19.16) | 29 | | 4.32 (1.56 - 11.97) | 29 | |
| 4 | 11.25 (3.54 - 35.69) | 43 | | 8.25 (2.62 - 25.92) | 35 | |
| PG | | | | | | |
| BMI adjusted | | | 0.589 | | | |
| 1 | 1.00 (Ref.) | 23 | | | | |
| 2 | 1.99 (0.89 - 4.44) | 35 | | | | |
| 3 | 1.60 (0.71 - 3.64) | 31 | | | | |
| 4 | 2.22 (0.93 - 5.29) | 34 | | | | |
| BMI, area adjusted | | | 0.661 | | | |
| 1 | 1.00 (Ref.) | 23 | | | | |
| 2 | 2.35 (0.99 - 5.59) | 35 | | | | |
| 3 | 2.30 (0.94 - 5.61) | 31 | | | | |
| 4 | 4.42 (1.62 - 12.08) | 34 | | | | |

*FIG. 3*

| x-y | | below the mean | | | above the mean | | | Comb |
|---|---|---|---|---|---|---|---|---|
| | | m | b | R | m | b | R | R |
| PG - PG$_{sd}$ | Case | 0.37±0.03 | 0.81 | 0.71 | 0.13±0.02 | 6.68 | 0.53 | 0.81 |
| | Control | 0.37±0.03 | 0.72 | 0.69 | 0.11±0.02 | 6.37 | 0.48 | 0.77 |
| area - PG$_{sd}$ | Case | -0.63±0.10 | 15.4 | -0.48 | -0.17±0.06 | 9.48 | -0.27 | -0.48 |
| | Control | -0.78±0.12 | 15.6 | -0.48 | -0.29±0.08 | 9.83 | -0.34 | -0.56 |
| area - PG | Case | -2.55±0.43 | 51.3 | -0.46 | -0.35±0.15 | 22.6 | -0.22 | -0.41 |
| | Control | -2.61±0.54 | 44.8 | -0.35 | -0.95±0.28 | 29.8 | -0.30 | -0.43 |

| Breast density measure | Cancer Side OR (95% CI) | Case | Az |
|---|---|---|---|
| BMI adjusted | | | 0.639 |
| 1 | 1.00 (Ref.) | 17/31 | |
| 2 | 2.166 (0.954 - 4.920) | 36/31 | |
| 3 | 1.107 (0.478 – 2.565) | 21/31 | |
| 4 | 3.483 (1.473 - 8.232) | 49/30 | |
| BMI, area adjusted | | | 0.719 |
| 1 | 1.00 (Ref.) | 17/31 | |
| 2 | 2.756 (1.109 - 6.850) | 36/31 | |
| 3 | 3.027 (1.035 - 8.854) | 21/31 | |
| 4 | 9.433 (3.101 – 28.698) | 49/30 | |
| BMI, area, t adjusted | | | 0.720 |
| 1 | 1.00 (Ref.) | 17/31 | |
| 2 | 2.757 (1.111 – 6.847) | 36/31 | |
| 3 | 3.047 (1.040 – 8.926) | 21/31 | |
| 4 | 9.570 (3.128 – 29.276) | 49/30 | |
| BMI, area, mAs adjusted | | | 0.720 |
| 1 | 1.00 (Ref.) | 17/31 | |
| 2 | 2.751 (1.106 – 6.842) | 36/31 | |
| 3 | 3.026 (1.035 – 8.849) | 21/31 | |
| 4 | 9.506 (3.101 - 29.140) | 49/30 | |

*FIG. 9*

| Characteristic | Case n | Case Mean/SD or % | Control n | Control Mean SD or % |
|---|---|---|---|---|
| Age | 160 | 58.5/10.6 | 160 | 58.5/10.5 |
| HRT | | | | |
| Never used | 84 | 52.5% | 88 | 55.0% |
| 1-5 years | 26 | 16.3% | 23 | 14.4% |
| 6-10 years | 17 | 10.6% | 17 | 10.6% |
| 11-15 years | 12 | 7.5% | 10 | 6.3% |
| >15 years | 21 | 13.1% | 22 | 13.8% |
| BMI (kg/m$^2$) | 159* | 26.4/4.5 | 160 | 25.3/4.3 |
| Breast area (pixels) | 160 | 1,392,643/478,251 | 160 | 1,318,957/407,717 |
| Menopausal (post) | 123 | 76.9% | 115 | 71.9% |

| Quartile OR (95% CI) | First ($n_1$) | Second ($n_2$) | Third ($n_3$) | Fourth ($n_4$) | Az |
|---|---|---|---|---|---|
| PD $n$ = 160 | 23 | 41 | 39 | 57 | |
| BMI adjusted | 1.00 (ref.) | 2.50 (1.12–5.56) | 2.85 (1.26–6.45) | 4.94 (2.10–11.62) | 0.630 |
| BMI, area adjusted | 1.00 (ref.) | 2.57 (1.15–5.75) | 2.87 (1.26–6.53) | 5.17 (2.17–12.33) | 0.637 |
| BMI, area, menopausal adjusted | 1.00 (ref.) | 2.70 (1.19–6.14) | 2.94 (1.27–6.80) | 5.24 (2.18–12.59) | 0.643 |
| $PG_{SD}$ $n$ = 160 | 22 | 53 | 38 | 47 | |
| BMI adjusted | 1.00 (ref.) | 3.36 (1.58–7.13) | 2.89 (1.24–6.74) | 4.84 (1.95–12.02) | 0.637 |
| BMI, area adjusted | 1.00 (ref.) | 3.80 (1.75–8.24) | 3.56 (1.46–8.69) | 6.18 (2.34–16.28) | 0.639 |
| BMI, area, menopausal adjusted | 1.00 (ref.) | 4.63 (2.05–10.47) | 4.26 (1.69–10.76) | 7.43 (2.72–20.28) | 0.651 |
| $R_{SD}$ $n$ = 160 | 26 | 42 | 41 | 51 | |
| BMI adjusted | 1.00 (ref.) | 1.81 (0.89–3.67) | 2.11 (0.97–4.61) | 2.78 (1.29–5.97) | 0.617 |
| BMI, area adjusted | 1.00 (ref.) | 2.07 (0.99–4.30) | 2.59 (1.13–5.94) | 3.48 (1.52–7.93) | 0.625 |
| BMI, area, menopausal adjusted | 1.00 (ref.) | 2.17 (1.03–4.57) | 2.86 (1.22–6.72) | 3.76 (1.62–8.70) | 0.634 |
| $R_{SDL}$ $n$ = 160 | 21 | 39 | 44 | 56 | |
| BMI adjusted | 1.00 (ref.) | 2.41 (1.15–5.08) | 3.39 (1.52–7.58) | 4.37 (1.94–9.85) | 0.636 |
| BMI, area adjusted | 1.00 (ref.) | 2.66 (1.24–5.68) | 3.82 (1.67–8.76) | 4.95 (2.14–11.46) | 0.646 |
| BMI, area, menopausal adjusted | 1.00 (ref.) | 2.89 (1.34–6.27) | 4.44 (1.88–10.49) | 5.38 (2.29–12.63) | 0.654 |
| $R_{SDX}$ $n$ = 160 | 24 | 55 | 36 | 45 | |
| BMI adjusted | 1.00 (ref.) | 2.96 (1.44–6.10) | 2.29 (1.06–4.95) | 3.57 (1.48–8.59) | 0.639 |
| BMI, area adjusted | 1.00 (ref.) | 3.35 (1.58–7.09) | 2.89 (1.26–6.64) | 4.74 (1.81–12.40) | 0.639 |
| BMI, area, menopausal adjusted | 1.00 (ref.) | 3.50 (1.64–7.47) | 3.11 (1.34–7.23) | 4.87 (1.85–12.84) | 0.650 |

FIG. 12

Patient Characteristics by Study and Case-Control Status.

| Variable | MMHS | | | MCBCS | | MCMAM | |
|---|---|---|---|---|---|---|---|
| | Subcohort | Control | Case | Control | Case | Control |
| Number of Women | 217 | 2094 | 928 | 1039 | 246 | 515 |
| Age at Mammogram | 55.3±10.7 | 51.6±11.0 | 59.3±11.8 | 61.4±11.0 | 64.9±10.1 | 64.1±10.2 |
| BMI | 28.2±5.7 | 27.7±6.7 | 27.6±5.6 | 27.0±5.3 | 27.9±5.0 | 27.5±5.2 |
| Menopausal Status | | | | | | |
| Pre | 93 (43%) | 1121 (54%) | 238 (25%) | 201 (19%) | 21 (8%) | 40 (8%) |
| Post | 124 (57%) | 973 (46%) | 676 (73%) | 831 (80%) | 223 (91%) | 471 (91%) |
| Unknown | 0 (0%) | 0 (0%) | 14 (2%) | 7 (1%) | 2 (1%) | 4 (1%) |
| Invasive cancer | 155 (71%) | | 748 (81%) | | 193 (78%) | |
| Percent Density | 21.6±15.3 | 19.7±15.1 | 27.4±15.1 | 21.4±14.0 | 22.5±15.0 | 18.3±13.6 |
| V | 383.3±145.1 | 305.33±125.1 | 435.3±146.5 | 311.5±109.3 | 320.4±126.3 | 285.0±115.8 |

*FIG. 16*

Association of Percent Density (PD) and Variation (V) Density Measures with Breast Cancer (and corresponding AUC) Adjusted for Age, BMI, and Menopausal Status

| Variable | MMHS | | MCBCS | | MCMAM | |
|---|---|---|---|---|---|---|
| | Subcohort | HR (95% CI) | Cases | OR (95% CI) | Cases | OR (95% CI) |
| PD quartiles | | | | | | |
| 1 (0-8.3) | 51 | Ref | 91 | Ref | 50 | Ref |
| 2 (8.4-17.6) | 52 | 1.48 (1.00, 2.19) | 179 | 1.61 (1.17, 2.21) | 50 | 1.16 (0.73, 1.85) |
| 3 (17.7-28.3) | 43 | 1.64 (1.06, 2.52) | 253 | 2.05 (1.50, 2.80) | 68 | 1.76 (1.11, 2.78) |
| 4 (28.4-79.4) | 71 | 3.12 (2.04, 4.79) | 405 | 4.39 (3.14, 6.13) | 78 | 3.09 (1.86, 5.12) |
| AUC | | 0.652 | | 0.642 | | 0.608 |
| Per 1 SD PD | 217 | 1.56 (1.33, 1.81) | 928 | 1.81 (1.61, 2.04) | 246 | 1.61 (1.33, 1.96) |
| AUC | | 0.649 | | 0.649 | | 0.614 |
| V quartiles | | | | | | |
| 1 (0-212) | 36 | Ref | 53 | Ref | 48 | Ref |
| 2 (213-280) | 22 | 0.92 (0.54, 1.56) | 109 | 1.33 (0.91, 1.94) | 65 | 1.67 (1.08, 2.60) |
| 3 (281-380) | 44 | 2.10 (1.34, 3.32) | 184 | 2.98 (2.07, 4.30) | 63 | 1.92 (1.22, 3.04) |
| 4 (381-809) | 115 | 6.96 (4.64, 10.42) | 582 | 10.70 (7.48, 15.31) | 70 | 2.62 (1.63, 4.20) |
| AUC | | 0.710 | | 0.746 | | 0.601 |
| Per 1 SD V | 217 | 2.39 (2.09, 2.73) | 928 | 3.12 (2.76, 3.53) | 246 | 1.48 (1.23, 1.78) |
| AUC | | 0.710 | | 0.764 | | 0.604 |

FIG. 17

Estimated Relative Risk for Meta Analysis Adjusted for Age, BMI, and Menopausal Status.

| Variable | MMHS | MCBCS | | MCMAM | | Meta Analysis |
|---|---|---|---|---|---|---|
| | HR (95% CI) | OR (95% CI) | ~RR (95% CI) | OR (95% CI) | ~RR (95% CI) | RR (95% CI) |
| PD quartiles | | | | | | |
| 1 (0-8.3) | Ref | Ref | Ref | Ref | Ref | Ref |
| 2 (8.4-17.6) | 1.48 (1.00, 2.19) | 1.61 (1.17, 2.21) | 1.35 (1.12, 1.62) | 1.16 (0.73, 1.85) | 1.11 (0.80, 1.55) | 1.31 (1.13, 1.52) |
| 3 (17.7-28.3) | 1.64 (1.06, 2.52) | 2.05 (1.50, 2.80) | 1.54 (1.30, 1.81) | 1.76 (1.11, 2.78) | 1.47 (1.10, 1.95) | 1.53 (1.34, 1.75) |
| 4 (28.4-79.4) | 3.12 (2.04, 4.79) | 4.39 (3.14, 6.13) | 2.11 (1.84, 2.43) | 3.09 (1.86, 5.12) | 1.99 (1.54, 2.57) | 2.20 (1.83, 2.64) |
| V quartiles | | | | | | |
| 1 (0-212) | Ref | Ref | Ref | Ref | Ref | Ref |
| 2 (213-280) | 0.92 (0.54, 1.56) | 1.33 (0.91, 1.94) | 1.24 (0.94, 1.64) | 1.67 (1.08, 2.60) | 1.45 (1.08, 1.94) | 1.26 (1.03, 1.55) |
| 3 (281-380) | 2.10 (1.34, 3.32) | 2.98 (2.07, 4.30) | 2.09 (1.69, 2.59) | 1.92 (1.22, 3.04) | 1.59 (1.18, 2.12) | 1.91 (1.59, 2.30) |
| 4 (381-809) | 6.96 (4.64, 10.42) | 10.70 (7.48, 15.31) | 3.47 (2.88, 4.17) | 2.62 (1.63, 4.20) | 1.91 (1.45, 2.51) | 3.52 (1.93, 6.43) |

FIG. 18

| Quartile | Case n=180 | unadjusted OR (95% CI) | BMI, area, menopause adjusted OR (95% CI) |
|---|---|---|---|
| | | $PG_1$ (or the $l_1$ norm) | |
| 1 | 26 | 1.00 (Ref.) | 1.00 (Ref.) |
| 2 | 67 | 2.37 (1.29, 4.34) | 4.29 (2.07, 8.90) |
| 3 | 34 | 1.31 (0.64, 2.69) | 3.10 (1.28, 7.54) |
| 4 | 53 | 2.12 (1.06, 4.24) | 6.56 (2.55, 16.90) |
| Az | | 0.599 | 0.662 |

*FIG. 20*

| Quartile | Case n=180 | BMI, area, menopause adjusted OR (95% CI) |
|---|---|---|
| | | $PG_1$ ($u_1$) controlling for $u_2$ |
| 1 | 26 | 1.00 (Ref.) |
| 2 | 67 | 4.04 (1.93, 8.46) |
| 3 | 34 | 3.04 (1.25, 7.43) |
| 4 | 53 | 7.98 (2.96, 21.57) |
| Az | | 0.670 |
| $u_2$ | | 1.53 (0.85, 2.73) |

*FIG. 21*

METHOD FOR ASSESSING BREAST DENSITY

This application claims priority to U.S. Provisional Application No. 61/423,390 filed Dec. 15, 2010, the disclosure of which is incorporated herein by reference.

STATEMENT REGARDING FEDERALLY FUNDED RESEARCH

This invention was made with Government support under Grant No. CA114491 awarded by the National Institutes of Health. The Government has certain rights in the invention.

FIELD OF INVENTION

This invention relates to a mammography; more specifically to methods of analyzing mammography results for estimating breast cancer risk for related applications such as for the detection of breast cancer.

BACKGROUND

Breast density is a significant breast cancer risk factor measured from mammograms. To date, most work in breast density has been performed with raw data using an operator assisted labeling method. Although breast density is a significant breast cancer risk factor, it is not currently used for risk assessments in a clinical setting, partly due to lack of standardization and automation. Evidence suggests that the spatial variation in mammograms may also be associated with risk. The variation in calibrated mammograms as a breast cancer risk factor was investigated and its relationship with other measures of breast density was explored using full field digital mammography (FFDM) as described herein. For additional discussion of the variation measure, see Heine, J. J. et al. "Calibrated measures for breast density estimation," *Acad Radiol*, vol. 18, pp. 547-55, May 2011; Heine, J. J. et al., "A Quantitative Description of the Percentage of Breast Density Measurement Using Full-field Digital Mammography," *Acad Radiol*, vol. 18, pp. 556-64, May 2011.

There are various methods used to assess breast density. For the most part, breast density and breast cancer associations have been developed with measurements that did not consider the inter-image acquisition technique differences. In particular, the operator-assisted percentage of breast density approach (or PD) has shown repeatedly to correlate well with breast cancer without considering the acquisition technique. Methods for automating PD are not widely used. An alternative method of assessing breast density is to calibrate, or adjust, for the acquisition technique differences.

Calibration should reduce unwanted measurement variation and produce a measure of mammographic density that shows stronger associations with breast cancer than non-calibrated methods such as PD. However, measurements based on calibration with digitized film mammography have produced mixed findings. Some work shows that calibration does not produce anything beyond PD. Other work shows that calibration strengthens the breast density associations with film mammography. For example, using FFDM, studies have shown that calibration can be used to both describe PD and to develop new measures of breast density. One new measure is calculated as the standard deviation (SD) of the calibrated pixels within the breast area, which captures spatial variation. This measure provided stronger associations with breast cancer than PD in some studies.

The calibration produces image data normalized for the inter-image acquisition technique differences at the pixel level (or more coarse scales) referred to as the percent glandular representation, which is a normalized effective x-ray attenuation coefficient metric. Differences in the compressed breast thickness, target/filter combination, x-ray tube voltage and exposure are rectified by the calibration process. There are many technical problems that if not addressed will introduce considerable error into the calibration output.

In one study, a matched case-control analysis was used to assess a spatial variation breast density measure in calibrated FFDM images, normalized for the image acquisition technique variation. Three measures of breast density were compared between cases and controls: (a) the calibrated average measure, (b) the calibrated variation measure, and (c) the standard percentage of breast density (PD) measure derived from operator-assisted labeling. Linear correlation and statistical relationships between these three breast density measures were also investigated.

Risk estimates associated with the lowest to highest quartiles for the calibrated variation measure were greater in magnitude [odds ratios: 1.0 (ref.), 3.5, 6.3, and 11.3] than the corresponding risk estimates for quartiles of the standard PD measure [odds ratios: 1.0 (ref.), 2.3, 5.6, and 6.5] and the calibrated average measure [odds ratios: 1.0 (ref.), 2.4, 2.3, and 4.4]. The three breast density measures were highly correlated, showed an inverse relationship with breast area, and related by a mixed distribution relationship.

The three measures of breast density capture different attributes of the same data field. These findings indicate the variation measure is a viable automated method for assessing breast density. Insights gained by this work may be used to develop a standard for measuring breast density.

SUMMARY

The present invention is directed to methods of assessing breast density for breast cancer risk assessment applications. The methods include receiving digital image data (including FFDM and digitized film as well as other forms of imaging) including a plurality of pixels; calibrating the digital image data; performing a statistical analysis on the calibrated digital image data; and associating the statistically analyzed digital image data with a measure of risk for breast cancer.

In accordance with one aspect of the invention, performing a statistical analysis may include calculating a mean of pixel values of the plurality of pixels.

In accordance with another aspect of the invention, performing a statistical analysis may include calculating a variation of pixel values of the plurality of pixels. For example, calculating a variation may be accomplished using at least one of a second central moment, a third central moment or a fourth central moment and including all central moments of integer and fractional order, where fractional implies a real number. Additionally, this includes all non-central moments of all order. Additionally, calculating a variation of pixel values of the plurality of pixels may include calculating the $l^2$ norm or the $l^1$ norm and all order moments derived from the $l^2$ and $l^1$ norm forms. Alternatively, a variation of pixel values of the plurality of pixels may include calculating combinations of the measures defined above. For example, calculating a combination measure based on results of the $l^1$ norm (i.e., $PG_1$) and the $l^2$ norm (i.e., $PG_2$) may be accomplished using the Gram-Schmidt orthogonalization process, Principal Component Analysis, partial least squares as well as nonlinear approaches and/or kernel based methods, but not limited to these combination method examples.

In accordance with an aspect of the invention, the digital image data may be raw image data obtained by digital mammography.

In accordance with another aspect of the invention, the digital image data may have been converted from mammography results recorded on film.

In accordance with an aspect of the invention, calibrating the digital image data may include adjusting for image acquisition technique parameters. For example, adjusting for image acquisition technique parameters may be accomplished by adjusting for at least one of variation in target/filter combination, x-ray tube voltage, radiation exposure and compressed breast thickness.

In accordance with one feature of the invention, calibrating the digital image data may be performed pixel-by-pixel. Alternatively, calibrating the digital image data may be performed by calculating an average pixel value of an n×n pixel region, and then calibrating the average pixel value.

In accordance with one aspect of the invention, the digital image data may be an image having a breast tissue area and a background area, and the method may further include segmenting the breast tissue area from the background area of the image. The breast tissue area may include adipose and glandular regions. In one example, segmenting may include assigning pixel values within the breast tissue area a first value and assigning pixel values within the background area a second value.

In accordance with another aspect of the invention, the method may include positioning a radial coordinate system origin at a side of the image at a first direction centroid position estimated from the segmented image.

In accordance with yet another aspect of the invention, the method may include eroding a percentage of the image between the radial coordinate system origin and the perimeter of the breast area along a radial direction.

In accordance with another aspect of the invention, the percentage is in a range between 0 and 35%. However, eroding a different percentage of the image may also be acceptable.

In second example implementation, methods include receiving digital image data (including FFDM and digitized film as well as other forms of imaging) including a plurality of pixels; performing a statistical analysis on the digital image data; and associating the statistically analyzed digital image data with a measure of risk for breast cancer.

In accordance with one aspect of the second example implementation, performing a statistical analysis may include calculating a variation of pixel values of the plurality of pixels. For example, calculating a variation may be accomplished using at least one of a second central moment (or square root of this moment), a third central moment, fourth central moment or all higher order central and non-central moments of all order including fractional or non-integer orders for all moments. We use fractional to include all real numbers. Calculating a variation of pixel values of the plurality of pixels may include calculating an $l^2$ norm and an $l^1$ norm and all orders using the $l^1$ norm form as the base. Alternatively, a variation of pixel values of the plurality of pixels may include calculating combinations of measures based on the results of the $l^2$ norm and the $l^1$ norm combination study. For example, combination methods may include the Gram-Schmidt orthogonalization process, Principal component analysis, partial least squares analysis as well as non-linear approaches and/or kernel based methods, but not limited to these combination methods.

In accordance with an aspect of the invention, the digital image data may be raw image data obtained by digital mammography.

In accordance with another aspect of the invention, the digital image data may have been converted from mammography results recorded on film.

In accordance with one aspect of the invention, the digital image data may be an image having a breast tissue area and a background area, and the method may further include segmenting the breast tissue area from the background area of the image. The breast tissue area may include adipose and glandular regions. In one example, segmenting may include assigning pixel values within the breast tissue area a first value and assigning pixel values within the background area a second value.

In accordance with another aspect of the invention, the method may include positioning a radial coordinate system origin at a side of the image at a first direction centroid position estimated from the segmented image.

In accordance with yet another aspect of the invention, the method may include eroding a percentage of the image between the radial coordinate system origin and a perimeter of the breast area along a radial direction.

In accordance with another aspect of the invention, the percentage is in a range between 0 and 35%. However, eroding a different percentage of the image may also be acceptable.

In accordance with a third example implementation of the invention, the methods may be implemented by a non-transitory computer-readable storage medium having computer-executable instructions stored thereon for assessing breast density for breast cancer risk applications by analyzing digital image data (including FFDM and digitized film as well as other forms of imaging) that, when executed by a processor, cause the processor to perform a statistical analysis on the digital image data; and associate the statistically analyzed digital image data with a measure of risk for breast cancer.

In accordance with one aspect of the invention, a statistical analysis may include calculating a mean of pixel values of the plurality of pixels.

In accordance with another aspect of the invention, a statistical analysis may include calculating a variation of pixel values of the plurality of pixels. For example, a variation may be calculated using at least one of a second central moment, a third central moment or a fourth central moment and including all order central and non-central moments, where the order includes all real number orders. Additionally, calculating a variation of pixel values of the plurality of pixels may include calculating the $l^2$ norm or the $l^1$ norm and all order moments derived from the $l^2$ and $l^1$ norm forms. Alternatively, a variation of pixel values of the plurality of pixels may include calculating combinations of the measures defined above. For example, calculating a combination measure based on results of the $l^1$ norm (i.e., $PG_1$) and the $l^2$ norm (i.e., $PG_2$) may be accomplished using the Gram-Schmidt orthogonalization process, Principal component analysis, partial least squares as well as nonlinear approaches and/or kernel based methods, but not limited to these combination method examples.

In accordance with an aspect of the invention, the digital image data may be raw image data obtained by digital mammography.

In accordance with another aspect of the invention, the digital image data may have been converted from mammography results recorded on film.

In accordance with yet another aspect of the invention, the non-transitory computer-readable storage medium may include further computer-executable instructions stored thereon that, when executed by the processor, cause the processor to calibrate the digital image data.

In accordance with an aspect of the invention, calibrating the digital image data may include adjusting for image acquisition technique parameters. For example, adjusting for image acquisition technique parameters may be accomplished by adjusting for at least one of variation in target/filter combination, x-ray tube voltage, radiation exposure and compressed breast thickness.

In accordance with one feature of the invention, calibrating the digital image data may be performed pixel-by-pixel. Alternatively, calibrating the digital image data may be performed by calculating an average pixel value of an n×n pixel region, and then calibrating the average pixel value.

In accordance with one aspect of the invention, the digital image data may be an image having a breast tissue area and a background area, and the method may further include segmenting the breast tissue area from the background area of the image. The breast tissue area may include adipose and glandular regions. In one example, segmenting may include assigning pixel values within the breast tissue area a first value and assigning pixel values within the background area a second value.

In accordance with another aspect of the invention, the method may include positioning a radial coordinate system origin at a side of the image at a first direction centroid position estimated from the segmented image.

In accordance with yet another aspect of the invention, the method may include eroding a percentage of the image between the radial coordinate system origin and a perimeter of the breast area along a radial direction.

In accordance with another aspect of the invention, the percentage is in a range between 0 and 35%. However, eroding a different percentage of the image may also be acceptable.

Additional features and advantages of the invention will be made apparent from the following detailed description of illustrative embodiments that proceeds with reference to the accompanying drawings. For example, in accordance with other aspects of the invention, the risk measure may include any combination of order measures discussed above.

BRIEF DESCRIPTION OF THE DRAWINGS

For a fuller understanding of the invention, reference should be made to the following detailed description, taken in connection with the accompanying drawings, in which:

FIG. 2 is a table of patient characteristics from a first example study;

FIG. 3 is a table of breast density measurements in association with breast cancer from the first example study;

FIG. 9 is a table of breast density measurements in association with breast cancer using raw mammograms without calibration from the first example study;

FIG. 12 is a table of breast density measurements in association with breast cancer from the second example study;

FIG. 16 is a table of patient characteristics from a third example study;

FIG. 17 is a table of breast density measurements in association with breast cancer from the third example study;

FIG. 18 is a table of meta-analysis from the third example study;

FIG. 20 is a table of breast density measurements in association with breast cancer using the $l^1$ (i.e., $PG_1$) vector norm; and FIG. 21 is a table of breast density measurements in association with breast cancer using a combination of the $l^2$ vector norm and the $l^1$ vector norm (i.e., $PG_2$ and $PG_1$ respectively).

DETAILED DESCRIPTION OF THE PREFERRED EMBODIMENT

Figure 1:
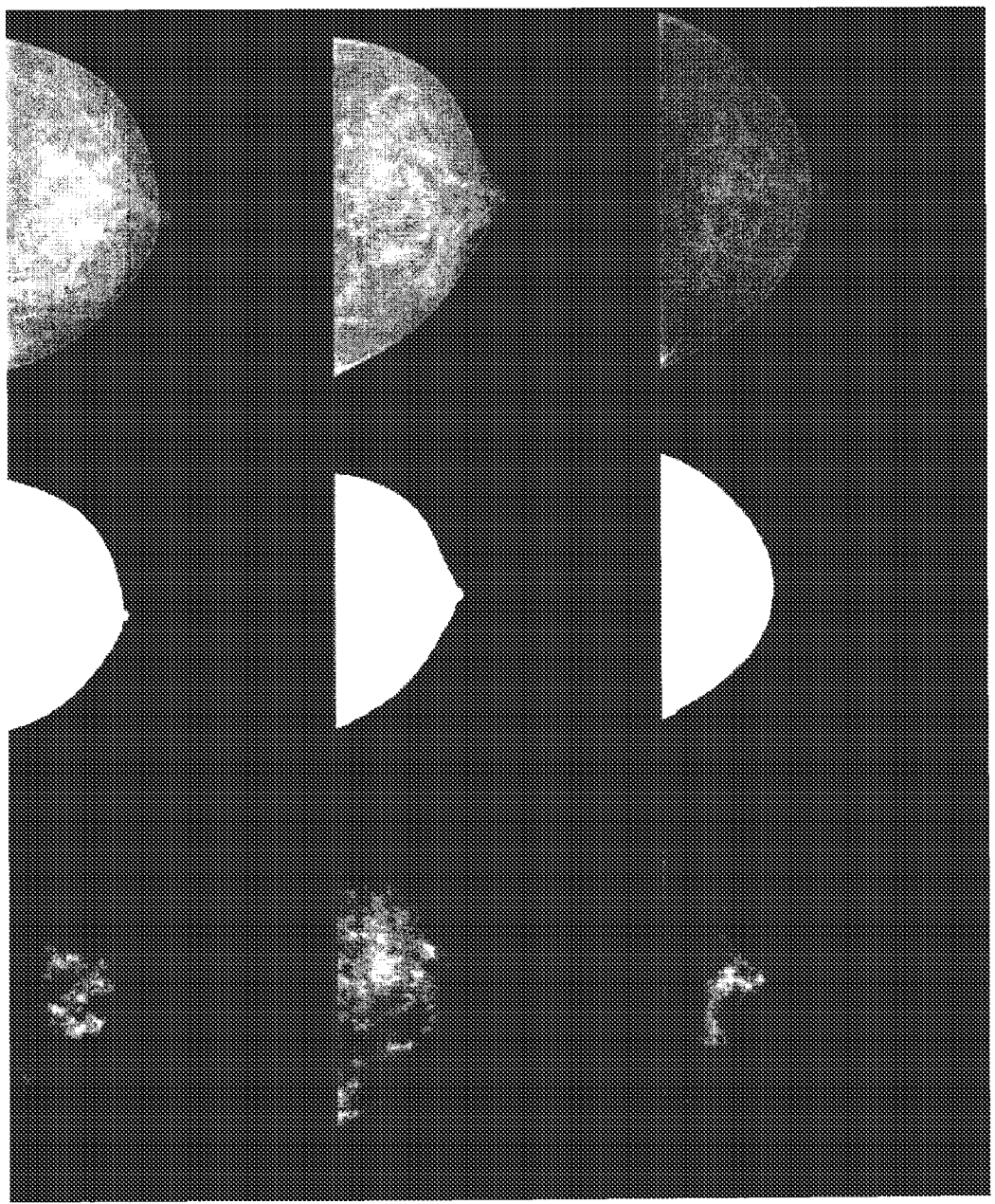
FIG. 1 illustrates example images created by a study FFDM unit used as raw image surrogates for display purposes only.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

First Example Study—Calibrated Measures for Breast Density Estimation

Introduction

Breast density measured from mammograms is a significant breast cancer risk factor. The association between breast density and breast cancer has been explored for many years. The earlier work in breast density used an observational four/five category rating of mammograms based on patterns of increasing risk. These earlier pattern measures of risk were virtually supplanted by the percentage of breast density (PD) measure developed by later researchers. More recently, the pattern analysis has gained attention using a different approach in comparison with the earlier observational methods. Rather than investigating the raw data directly, mammographic patterns (or projected breast structure) have been investigated with various textural related measures. For the most part, these are summary measures that include fractal analysis, features generated from applying various filtering methods, and co-occurrence features. Some of these measures show associations with breast cancer similar to that of the standard PD measure.

There are various methods used to assess breast density. The operator-assisted PD measure has demonstrated repeatedly to correlate well with breast cancer without considering the x-ray imaging acquisition influences. Another approach involves calibrating for the inter-image acquisition technique variation to produce normalized data representations. There is little published work showing the efficacy of calibrating mammograms for breast cancer risk assessments using breast cancer status as the endpoint comparison. Some work indicates that calibration measures do not produce stronger breast cancer associations than that of the standard operator-assisted PD measure. Other work indicates calibration may be useful for describing the information captured by the PD measure and for automating its measurement. If calibration can be optimized to improve the precision with which breast density is measured, a more accurate estimate of the magnitude of association between breast density and breast cancer may be obtained.

Here, the spatial variation in mammograms that were calibrated to account for the x-ray acquisition technique differences was investigated using FFDM. The calibration method was developed previously. See Kaufhold, J. et al., "A calibration approach to glandular tissue composition estimation in digital mammography," *Med Phys, vol.* 29, pp. 1867-80, August 2002. The calibration adjusts for variations in the target/filter combination, x-ray tube voltage, radiation exposure, compressed breast thickness, etc. to produce a normalized pixel value representation referred to as percent glandular (PG) that is equivalent to a normalized effective x-ray attenuation coefficient representation spanning this pixel value range (0-100). The calibration can be applied at the pixel or local level, which supports analyzing the calibrated pixel distribution characteristics within a given image.

For example, the calibration methods based on phantom imaging were initially developed without patient data. See Heine, J. J. et al., "Effective x-ray attenuation coefficient measurements from two full field digital mammography systems for data calibration applications," *Biomed Eng Online*, vol. 7, p. 13, Mar. 28 2008; Heine, J. J. et al., "Effective x-ray attenuation measurements with full field digital mammography," *Med Phys*, vol. 33, pp. 4350-66, November 2006. Calibration curves were developed as a function of the acquisition technique, such as target/filter combination, x-ray tube voltage, radiation exposure, compressed breast height, etc. For example, to calibrate a mammogram, the acquisition technique parameters are read from the image header-file, and then the proper mapping from the calibration curves are found. The calibration methodology requires rigid breast tissue equivalent (BTE) phantoms. The calibration curves were developed from imaging these BTE phantoms. The BTE nomenclature implies these phantoms attenuate x-rays for the energies used in mammography equivalent with their respective breast tissue counterparts (equivalent implies similar to and not exact). The BTE phantoms are rigid, have a large surface area that substantially covers the detector, and have exact heights (1 mm, 2 mm, 1 cm, and 2 cm). Combinations of these are used to span compression heights ranging from 1 mm through 7 cm, for example. 100% adipose and 100% glandular BTE phantoms were purchased from Computerized Imaging Reference Systems (CIRS, Norfolk Va.) for use in the study.

Additionally, preliminary validation (again without patient imaging) of the calibration principle used an alternative two-component system (alternative to the adipose—glandular two-component system discussed above) with deformable phantoms (i.e., water balloons) filled with water and oil. This alternative two-component system was utilized along with a method to correct for the breast compression height variation (or error). See Heine, J. J. et al., "Effective radiation attenuation calibration for breast density: compression thickness influences and correction," *BioMedical Engineering Online*, vol. 9, p. 73, 2010.

In addition, the compression paddle bulge and warp were modeled with the deformable phantoms. To model the slant on the compression paddle, additional modified (i.e., customized) BTE phantoms from CIRS were purchased. CIRS beveled one face of the phantoms (slant phantoms) with various inclination angles.

The calibration may also require a serial quality control monitoring system. See Heine, J. J. et al., "Cumulative Sum Quality Control for Calibrated Breast Density Measurements," *Medical Physics*, vol. 36 pp. 5380-5390, December 2009. Additionally, the calibration may require methods of updating the calibration curves to account for serial drift in the mammography unit (i.e., systematic drift in the detector, x-ray tube, or combination of both). This serial updating maintains the prospective calibration accuracy.

Materials and Methods

A matched case-control study was performed. Three breast density measures and their association with breast cancer were compared: (a) the average of the calibrated mammograms [the PG measure], (b) the standard deviation of the calibrated mammograms [the $PG_{sd}$ variation measure], and (c) the standard PD measure derived from the raw data (no calibration) using an operator-assisted labeling approach. The measurement correlation with (projected) breast area and the inter-measure correlation were also investigated. Breast area was used as a surrogate for breast size. The empirical probability distributions for the calibrated fibroglandular (abbreviated as glandular hereafter) and adipose tissue components were constructed. These component distributions were used to develop a statistical relationship between the three measures of breast density using a mixed distribution model. The variation measure was also investigated by calculating the standard deviation of the pixel values from the eroded breast area of the raw image (without calibration) for comparison purposes.

Materials and Methods: Study Population

A description of the study population is provided. All study images were acquired with one FFDM system. Controls were individually matched on age, hormone replacement therapy (HRT), and screening history to control for possible confounding influences. Breast cancer cases (n=123) were identified from the pool of women attending the breast clinics at the H. Lee Moffitt Cancer Center in Tampa, Fla. To be included as cases in the study, women had to have been diagnosed with a first-time unilateral breast cancer (September 2007-July 2010). For the purpose of matching controls to cancer cases, three groups of cases were considered based on their screening history. Group-1 was comprised of women that screened normal within 30 months prior to their breast cancer diagnosis ($n_1$=107). Group-2 was comprised of women who had a history of normal screening that fell outside of the group-1 parameters, such as a woman who had a screening in 2007 but not again until 2010 at which time she was diagnosed with cancer ($n_2$=12). Group-3 was comprised of women who were just beginning screening and were diagnosed at their baseline mammogram ($n_3$=4). Case data and images were either located by retrospective records review (n=40) for those women with images archived on the study FFDM unit or recruited, consented, and imaged for the study (n=83). The recruited case patients were those women found to have breast cancer at screening clinics in the surrounding area that were referred to the Moffitt Center for diagnostics or patients that were found to have breast cancer at the Moffitt Center that did not have mammograms archived on the study FFDM unit. Recruited case participants were given a standard screening type mammogram with the study FFDM unit before their treatment commenced. Cancer status was histologically verified for all cancer cases. Height, weight, and HRT usage were abstracted from patient records.

Controls (n=123) were identified from the pool of women undergoing breast cancer screening mammography at the H. Lee Moffitt Cancer Center with the study FFDM unit. Controls were age matched (±2 years), HRT usage/duration matched, and screening history matched with the cancer cases using the three screening categories discussed above. For HRT matching, non-users were defined as those women who never used HRT as well as those that stopped using HRT two years or more prior to when their study mammograms were acquired. For current users, HRT usage duration (±1 year) was used as a control matching variable. All control data and images were located retrospectively by records review over the same timeframe as the cases and restricted to women with screening mammograms available on the study FFDM unit. These archived mammograms were used as study images. Height, weight, and HRT usage were abstracted from patient records.

Here, two statistically similar datasets derived from the same patients for the various explorations were used. These are referred to as the cancer side and non-cancer side datasets. In the cancer side dataset, the cancerous breast of a given case was matched with the ipsilateral breast of the control. In the non-cancer side dataset, the non-cancerous breast of a given case was matched with the ipsilateral breast of the control. The combined dataset consisting of both the cancer side and non-cancer side datasets is referred to as the expanded dataset below. The expanded dataset was used for the correlation and distribution modeling investigations. The study protocol and informed consent process were approved by the local Institutional Review Board (IRB). This protocol is reviewed annually.

Materials and Methods: Imaging System

One General Electric Senographe 2000D FFDM system was used for this work. This mammography unit is used for routine breast cancer screening at the Moffitt Center. This system has a 100 µm digital spatial resolution. Craniocaudal (CC) views were used in this analysis to reduce chest muscle interference. The system produces both raw data and processed data for clinical display use. Raw data was used in the analyses (not processed data for clinical viewing). The system processed images (clinical display images) were used as raw image surrogates to provide display illustration examples. For example, FIG. 1 illustrates example images created by a study FFDM unit used as raw image surrogates for display purposes only. From left to right, the top row shows three processed images created by the study FFDM unit used as raw image surrogates for display purposes only. The middle row from left to right shows the corresponding segmented and then eroded breast image areas. The bottom row shows the corresponding percent glandular (PG) calibrated images. As in film mammograms, larger pixel values imply greater x-ray attenuation and greater breast density. For the bottom row from left to right, the measured (PG, $PG_{sd}$) values for each image were: (14.3, 5.8), (27.5, 5.4), and (14.9, 5.1), respectively. The raw image data is not useful for display purposes without considerable manipulation.

Materials and Methods: Calibrated Breast Density Measures

The PG calibration may be applied automatically at a lower resolution by averaging over 10×10 pixel regions, for example, to reduce unwanted variation. The PG and $PG_{sd}$ measures were determined by calculating the average and standard deviation of the calibrated pixel values within the breast area (defined below) for each image.

As discussed above, variation measures (i.e., $PG_{sd}$) used the standard deviation. In this study, the variation measure used the standard deviation of calibrated pixel values. However, as discussed below, the variation measure may use the standard deviation of the non-calibrated pixel values. In one implementation, the variation measure may be derived using the conventional standard deviation calculation:

$$PG_2 = PG_{sd} = \left[\frac{1}{q}\sum_{j=1}^{q}(pv_j - m)^2\right]^{\frac{1}{2}},$$

where $pv_j$ are the pixel values within the eroded breast area, m is the average (or mean) of $pv_j$, and there are q pixels within the eroded breast region. The expression applies to either calibrated $pv_j$ or non-calibrated $pv_j$ and applies to a given image. Naturally, both q and m vary from image to image (i.e., patient to patient). The above equation is an $l^2$ vector norm. Alternatively or additionally, it may be possible to use the $l^1$ vector norm to calculate variation defined as:

$$PG_1 = \frac{1}{q}\sum_{j=1}^{q}|pv_j - m|,$$

using the same definitions discussed above. Preliminary findings from 180 case-control pairs following from the selection and matching criteria described previously are presented in FIG. 20. Fractional order or non-integer order moments can be derived from these expressions by taking the absolute value of either expression within the summation argument and raising it to the said order. For example, substituting this expression $|pv_j-m|^x$ in the $PG_1$ equation or changing the numeral "2" in the $PG_2$ expression to x in both places, where x is any real number. Non central moments of any order follow from setting m=0. $PG_2$ is $PG_{sd}$ re-labeled. When using the $l^2$ form, it is not always required to use the absolute value for each term within the sum before raising the term to a given power. The absolute value operation depends on making the argument a valid expression required to raise it to a given power or the desired outcome. For example, skewness may be calculated by replacing the inner power 2 with 3 in the $l^2$ expression. The sum can be negative, in which case the sum would not be raised to the ⅓ power. There may be other situations where the term ($pv_j$–m) is negative and raising it to an arbitrary power of this from $(pv_j-m)^x$ may not be a valid expression with the $l^2$ form. In this case, taking the absolute value of every term in the sum for the given x is required when building on the $l^2$ norm form, and using the sum or raising the sum to 1/x power as the measure in all situations.

FIG. 20 shows the odds ratios (ORs) by quartile, the number of breast cancer cases samples (n) in each quartile for the $PG_1$ breast density measure. The first quartile was used as the reference (Ref.) for the seconds-fourth quartiles and 95% confidence intervals (CIs) are provided for each OR parenthetically. The area under the receiver operating characteristic curve (Az) is also provided. The findings are presented unadjusted form (left) and adjusted (right) for body mass index (BMI), breast area (area) and menopausal status. The strength of the measure is demonstrated by the associations in the right column.

FIG. 21 is a table with the combined measure findings. Further, a variation of pixel values of the plurality of pixels may include calculating combinations of the measures defined above. For example, calculating a combination measure based on results of the $l^1$ norm (i.e., $PG_1$) and the $l^2$ norm (i.e., $PG_2$) may be accomplished using the Gram-Schmidt orthogonalization process, Principal component analysis, partial least squares as well as nonlinear approaches and/or kernel based methods, but not limited to these combination method examples.

Referring to FIG. 21, the components of $u_1$ represent the $PG_1$ risk factors for each patient. The vector $u_2$ is $PG_{sd}$ with its projection along $PG_1$ (or $u_1$) removed. The components of $u_2$ are the modified $PG_{sd}$ risk factors for each patient with the $PG_1$ influence removed. FIG. 21 gives the odds ratios (ORs) by quartile and the number of breast cancer cases samples (n) in each quartile for the Gram-Schmidt analysis. The quartile findings for $PG_1$ while controlling for $u_2$ as a continuous variable are provided. The first quartile was used as the reference (Ref.) for the second-fourth quartiles and 95% confidence intervals (CIs) are provided for each OR parenthetically. The area under the receiver operating characteristic curve (Az) is also provided for each measure. The continuous OR is also provided for $u_2$ (bottom row). The model was adjusted for body mass index (BMI), breast area (area) and menopausal status. When comparing these findings with those in FIG. 20, the combination measure provides some gain in OR associations and in Az.

In addition to obtaining variation measures using the $l^2$ vector norm and the $l^1$ vector norm, it may be possible to obtain variation measures using other moments, such as the first central moment (average), the second central moment (or the square root of variance which is $PG_{sd}$), the third central moment (skewness), the fourth central moment (kurtosis), etc, or non-central moments, including moments of all order, and combinations of all measures. Hybrid measures include combinations of all of these measures. The order includes all real numbers.

Related work showed that eroding the breast area produces an image coincident with where the breast was in contact with the compression paddle. The breast area was first segmented from the background automatically by setting all pixels within the breast area to one (1) and setting all other pixels to zero (0). A radial coordinate system origin was positioned at the side of the image (chest wall position—left side in a left CC view) at the vertical direction (parallel to the chest wall) centroid position estimated from the segmented binary image. The breast area was then eroded by 25% of the distance measured from the radial coordinate system origin to the breast perimeter along a given radial direction. The breast area may be eroded by any percentage of the distance measured from the radial coordinate system origin to the breast perimeter along a given radial direction, but preferably in a range between 0 and 35% but not limited to this range. The calibration requires an accurate spatial assessment of the compressed breast thickness and therefore does not apply in the region where the breast is not in contact with the compression paddle because the thickness is unknown in this region. The erosion operation produces the portion of the image that approximates the region where the compressed breast thickness is defined and known. FIG. 1 shows three raw image surrogates. The corresponding eroded segmented images are shown in the middle row of FIG. 1. Both the average PG and $PG_{sd}$ measures were calculated from the region in the calibrated mammograms corresponding to eroded area. The respective calibrated (eroded) image examples are shown in the bottom row of FIG. 1.

Materials and Methods: Operator-Assisted Breast Density Measurements

The standard PD measurements were generated with the Cumulus3 (CM) software (University of Toronto) using the batch file procedure operating on the raw (non-processed images) FFDM images. The dataset consisting of all cases-control images (left and right CC view images) were first de-identified and randomized. The CM operator was blinded to the case-control status and original image identifiers. To avoid operator fatigue, the PD labeling was performed in multiple reading sessions (490 images were labeled). Hereafter, we use PD measure to refer to the standard breast density measurement derived from the CM labeling. This labeling technique can be considered as the de facto standard.

Materials and Methods: Statistical Analysis

Conditional logistic regression was used to assess the association between the three measures of breast density and the case-control status. A standard quartile analysis was used for the odds ratio (OR) comparisons, where the control breast density distribution was used to determine the cutoff value for each measure. The first quartile of breast density for each measure served as the reference group for the second through fourth quartiles. The quartile analysis also provided a means for comparing the inter-measure OR distributions. Body mass index (BMI) measured in kg/m$^2$ and breast area (pixel units) in the analyses were adjusted for as continuous variables. The area under the receiver operator characteristic curve (Az) metric was also used for predictive capability comparisons. This analysis was performed with the SAS software package (SAS Institute Inc., Cary, N.C.).

Linear regression analysis was used to investigate the inter-breast density measurement association and their relationship with the projected breast area. All relationships were fitted to the y=mx+b standard form. The full projected breast area (un-eroded breast area) was used in the analysis. This regression analysis was stratified by case-control group for comparisons of the calibrated measures using the expanded dataset.

Materials and Methods: Breast Density Statistical Model

To develop a model that explains the relationships between the three measures of breast density, the empirical probability distributions (estimates) for the combined case-control glandular and adipose tissue components were constructed and investigated (expanded dataset). These two components were used to formulate a mixed distribution that connects the standard PD, PG and $PG_{sd}$ breast density measures. It was shown previously that a PD-like measure ($PD_c$) of breast density can be generated from the calibrated PG representation (eroded) images automatically by first applying a data transform. Letting pg(x, y)=PG(x, y)/100, where PG(x, y) is the calibrated image pixel value located at the (x, y) spatial coordinates. Note that the pg(x,y) pixel values are constrained to this range (0,1). The normalized attenuated x-ray exposure representation image is then defined as $$A(x,y)=k(1.0-\exp[-pg(x,y)t_s]), \quad (1)$$

where $t_s$ is the system compressed breast thickness readout quantity expressed in cm for each image, and k=5000 is an arbitrary constant. Using $A_c$=3200 as a static threshold, pixel values within the eroded breast region meeting this condition $A(x,y) \geq A_c$ were counted as glandular pixels (the $d_n$ count), whereas pixel values meeting this condition $A(x,y)<A_c$ were counted as adipose regions (the $a_n$ count). For a given image, the PD-type measure is given by $$PD_c = \frac{d_n}{N} \times 100\% \text{ with } N = d_n + a_n.$$

It was shown previously that the $PD_c$ measure association with breast cancer is similar to that of the PD measure when analyzing the same dataset. For this work, the $PD_c$ labeled images were generated as an intermediate step to construct the component distributions. These binary labeled $PD_c$ images were then used as overlays for their respective PG representation images. For a given pair of $PD_c$ and PG images, regions (pixel values) in the PG image corresponding to the regions in the $PD_c$ image labeled as were assembled into an array. This process was carried out for every PG and $PD_c$ image pair in the extended dataset resulting in one array containing all PG pixel values corresponding to the labeling. The same process was carried out for the $a_n$, labeled regions resulting in another array. Normalizing each histogram of these arrays separately to unity gives an approximation for the respective ensemble probability distribution for each tissue type.

These two component distributions were used to formulate a mixed distribution relationship for each mammogram. For a two component mixture, the mixed distribution for a given image can be expressed as $$p(z) = c \times p_1(z) + (1-c) \times p_2(z), \quad (2)$$

where $p_i$ represents the component distributions (derived from the two arrays referenced above) with i=1 for the glandular component and i=2 for the adipose component, c is the two-component mixing proportion, and z=PG (calibrated pixel values). For a given image, the mean can be expressed as $$m = c \times m_1 + (1-c) \times m_2, \quad (3)$$

where $m_1$ and $m_2$ are the respective means determined from the component distributions. Likewise, the variance for a given image can be expressed as $$\sigma^2 = c \times (\sigma_1^2 + m_1^2) + (1-c) \times (\sigma_2^2 + m_2^2) - m^2, \quad (4)$$

where $\sigma_i$ represents the respective standard deviations calculated from the component distributions, and m was defined in Eq. (3). Equations (3-4) redefine the PG and $PG_{sd}$ breast density measures respectively and show the theoretical connection between the three breast density measures. The relationship with PD follows from Eq. (3). For a given image, $c \times 100\%$ is an approximation of the PD measure. The mixing proportion, c, theoretically accounts for the fraction of pixels within the breast area that would be labeled as dense breast tissue by the standard PD measure. Quantities $m_1$, $m_2$, $\sigma_1$, $\sigma_2$ were calculated from the respective component distributions. These quantities were then used with Eqs. (3-4) to estimate the mixing coefficient breast density measure, c, for each image using the respective PG and $PG_{sd}$ measures as substitutes for m and $\sigma$. A brief analysis of the $PD_c$ and the mixing coefficient measures of breast density was provided to demonstrate the validity of (a) the methods used to generate the component distributions, and (b) the Eq. (4) approximation.

Results

Results: Breast Density Measurement Comparisons

Demographic and risk factor distributions are provided for the breast cancer cases and controls in the shown in FIG. 2. Referring to FIG. 2, the number (n) of patients and percentages are provided for the breast cancer cases and controls stratified by hormone replacement therapy (HRT) usage and duration by years (yrs) of usage. The parenthetical entries cite current HRT users as defined in Study Population section above. The mean body mass index (BMI), age, and breast area are given for each group. The associated standard deviations (SDs) for the BMI, age, and breast area distributions are also provided.

Associations between the three breast density measurements (PD, $PG_{sd}$, and PG) and breast cancer are summarized in FIG. 3 (left-side) for the cancer side dataset. Specifically, FIG. 3 shows the association with breast cancer for the percentage of breast density (PD), the average calibrated (PG), and the calibrated standard deviation ($PG_{sd}$) measures of breast density. The odds ratios (OR), OR confidence intervals (CI), and area under the receiver operator characteristic curve (Az) values are also shown. The findings for the cancer-sided (left column) and non-cancer side (right column) are shown separately. One case image and one unrelated control image were not usable; therefore two case-control pairs were discarded. All measures were either adjusted for body mass index (BMI) measured in kg/m² and for BMI and area (pixel units), simultaneously. In FIG. 3, the OR associations and Az quantities were adjusted for BMI and the simultaneous adjustments for both BMI and breast area (i.e., the mammogram-based two-dimensional measure of breast size). For all three measures, the ORs and Az quantities increased (increased magnitude of association) when controlling for area. Both the PD and $PG_{sd}$ measures showed significant magnitude of association with breast cancer for all non-referent quartiles (i.e., the left side OR confidence intervals are greater than unity). In contrast, the confidence intervals for the PG measure included unity for most quartiles. The $PG_{sd}$ measure showed greater magnitude of association with breast cancer when comparing its quartile ORs with the other measures, and the PD measure showed greater association than the PG measure. The $PG_{sd}$ and PD measures produced similar Az values that were larger than that produced by the PG measure.

FIG. 9 shows the variation measure estimated from the raw mammograms. Specifically, FIG. 9 is a table of breast density measurements in association with breast cancer using raw mammograms without calibration from the first example study. FIG. 9 shows the cancer-side 123/123 case/control findings for the raw data. The measurement is the standard deviation of the pixel values within the eroded breast region. All measures were either adjusted for body mass index (BMI) measured in kg/m², for BMI and area (pixel units), for BMI, area and t, and for BMI, area, and mAs. Although the odds ratios are a bit lower than those calculated from the calibrated mammograms, they were derived from raw images with much less effort. The calibration requires a significant infrastructure support with phantom imaging and extensive analysis. In contrast, the raw image analysis requires little effort. In any event, the analysis (calibrated image or not), does not require user input (no operator dependent thresholds). The Az is slightly greater than the corresponding cancer side $PG_{sd}$ findings, whereas the ORs show greater magnitude of association for the non-referent quartiles for the $PG_{sd}$ measure (the calibrated measure). Thus, FIG. 9 shows that the non-calibrated measures may also be a strong measure of risk.

To assess whether the presence of breast abnormalities in the cancer side breast was responsible for the positive associations between breast cancer and the $PG_{sd}$ measure, the associations were investigated using the non-cancer side dataset. For comparison purposes, the non-cancer side analysis was performed for the PD measure for internal control comparisons. The findings are shown in FIG. 3 (right-side).

The OR associations and Az values decreased for both measures in comparison with the cancer-side dataset, but the inter-measure relationships remained similar.

Because the breast area for the cancer cases was larger than that of the controls (FIG. 2), a sub-group analysis was performed by ordering the cancer-side case samples by ascending breast area. Starting with the case-sample with the largest breast area, each case and associated control were removed from the 123 pairs one pair at a time until the case and control group breast areas were statistically similar. A paired t-test was used to compare the remaining case-control pair breast areas after discarding a given pair. When the set was reduced to between 100-110 matched pairs, the t-test began to lose significance. The choice of 100 matched pairs (P=0.87) was arbitrary (104 case/control pairs would work as well). When these case-control pairs (n=23) were excluded from the analysis, similar results were observed (data not shown).

Results: Correlation Comparisons

Figures 4, 5:
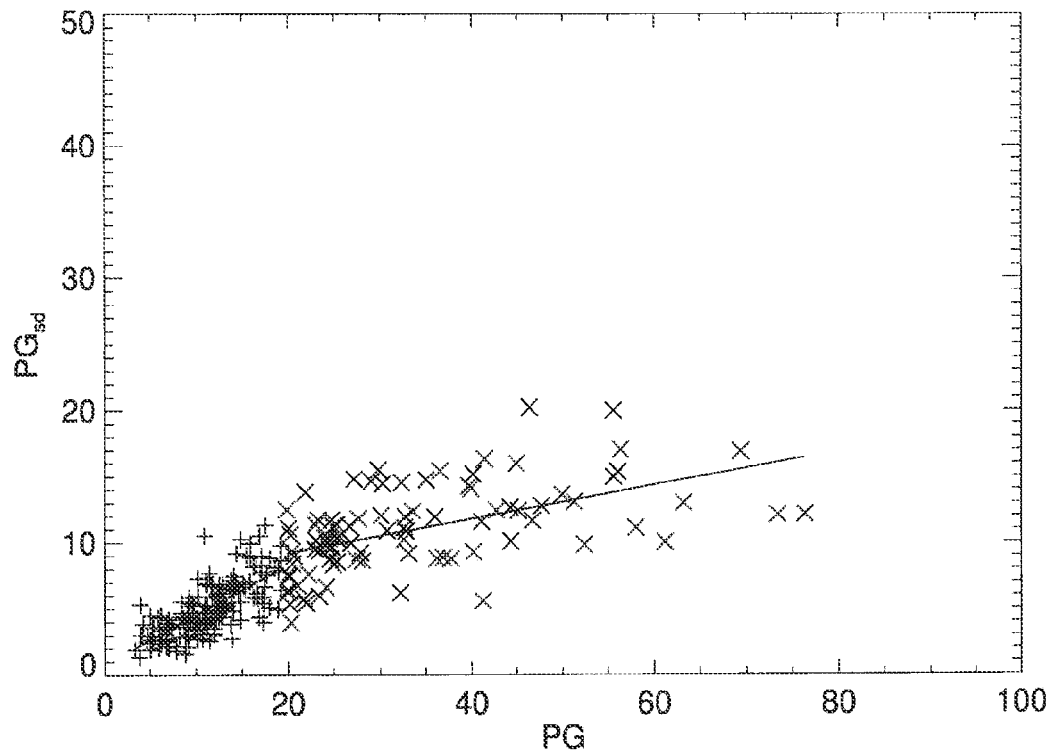
FIG. 4 is a graph illustrating the percent glandular breast density measure and the percent glandular standard deviation breast density measure regression analysis from the first example study.
FIG. 5 is a table of regression parameters for cases and controls from the first example study.

The (PG, $PG_{sd}$) regression plot for the cancer cases is shown in FIG. 4. Referring to FIG. 4, the percent glandular (PG) and PG standard deviation ($PG_{sd}$) ordered pairs and fitted lines (solid) are shown for the case samples of FIG. 5. The regression analysis was split into two parts for above (×) and below (+) the case PG distribution mean. Because of the apparent nonlinear trend, the analysis was divided into (PG, $PG_{sd}$) pairs that were either (a) equal to, or above, the case PG distribution mean, or (b) below this mean. A similar analysis was performed for the control (PG, $PG_{sd}$) pairs using the control PG measure distribution mean as the breakpoint. The regression plot for the controls is not shown due to close similarities with FIG. 4. The regression analysis is summarized in FIG. 5. Referring to FIG. 5, the two-part regression analysis summary fit to the form y=mx+b. The x-y pairs are shown in the first column. PG is the calibrated average measure, $PG_{sd}$ is the PG standard deviation measure, and area is the projected (not eroded) breast area. The distribution mean value of x was used as the breakpoint for each pair. The linear correlation coefficient (R) is shown for each line segment and the combination (Comb) correlation is cited in the last column, derived without the breakpoint. The PG distribution mean and standard deviation (mean, SD) for the cases and controls were: (19.8, 13.9) and (18.5, 13.7), respectively. The breast area summaries are provided in FIG. 2. Comparisons of the regression parameters and linear correlation coefficients indicate the cases and controls exhibit similar behavior. The overall correlation without considering the break also showed that the cases and controls behave similarly (last column of FIG. 5). The correlation between the PD and PG measures was R=0.76, and the correlation between PD and $PG_{sd}$ measures was R=0.78, as determined with the extended dataset (not shown).

Figure 6:
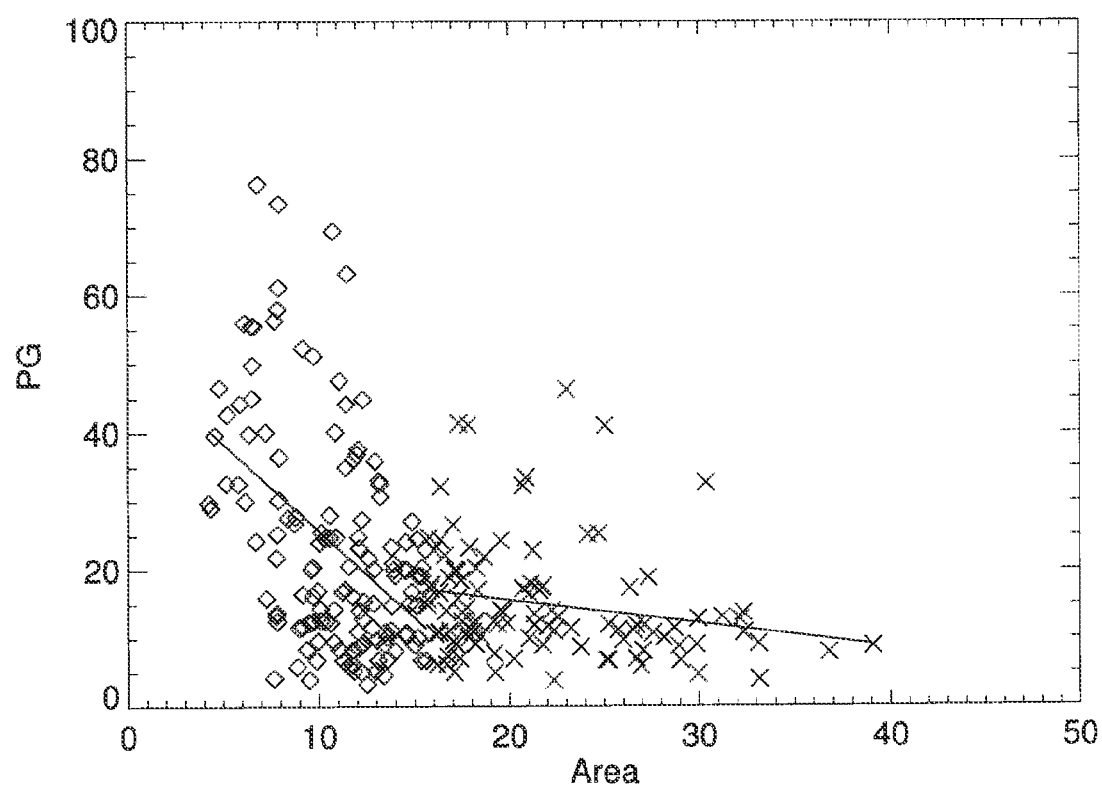
FIG. 6 is a graph illustrating the breast area and the percent glandular breast density measure regression analysis from the first example study.
Figure 7:
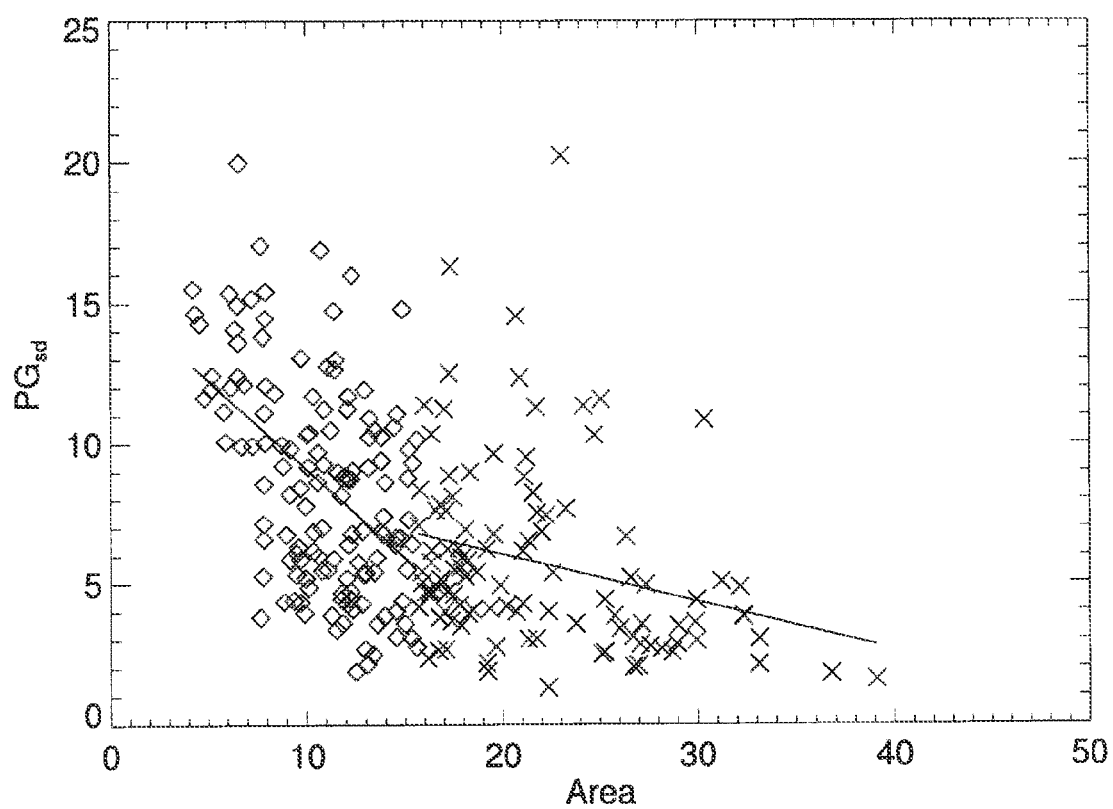
FIG. 7 is a graph illustrating the breast area and the percent glandular standard deviation breast density measure regression analysis from the first example study.

The correlation between the breast density measurements and breast area was investigated. FIG. 6 shows the (area, PG) regression plot for the cancer cases. Referring to FIG. 6, the graph shows breast area (area) expressed in $10^5$ pixel units and percent glandular measure (PG) ordered pairs and fitted lines (solid) for the case samples of FIG. 5. The regression analysis was split into two parts for above (×) and below (diamond) the case breast area distribution mean. This analysis was also divided into (area, PG) pairs using the same format as above that were (a) either equal to, or above, the case breast area distribution mean, or (b) below this mean (Table 1). FIG. 7 shows the (area, $PG_{sd}$) regression plot using the same mean area break point. Referring to FIG. 7, the graph shows the breast area (area) expressed in $10^5$ pixel units and the percent glandular standard deviation measure ($PG_{sd}$) ordered pairs and fitted lines (solid) for the case samples (Table 3). The regression analysis was split into two parts for above (×) and below (diamond) the case breast area distribution mean. The two measures show similar correlation with area. A similar analysis was performed for the control PG and $PG_{sd}$ measures with breast area using the control area distribution mean as the break point (not shown). The breast density measurement and breast area regression analysis findings are summarized in FIG. 5. The correlations and relationships were stronger and more similar across case-control group for the below mean-area groups. Using the extended dataset with no break point, the (area, PD) correlation was R=−0.39. The degree of the negative correlation between the breast density measures and breast area suggests that area should be controlled in the association analysis as shown in FIG. 3.

Results: Statistical Model Evaluation

Figure 8:
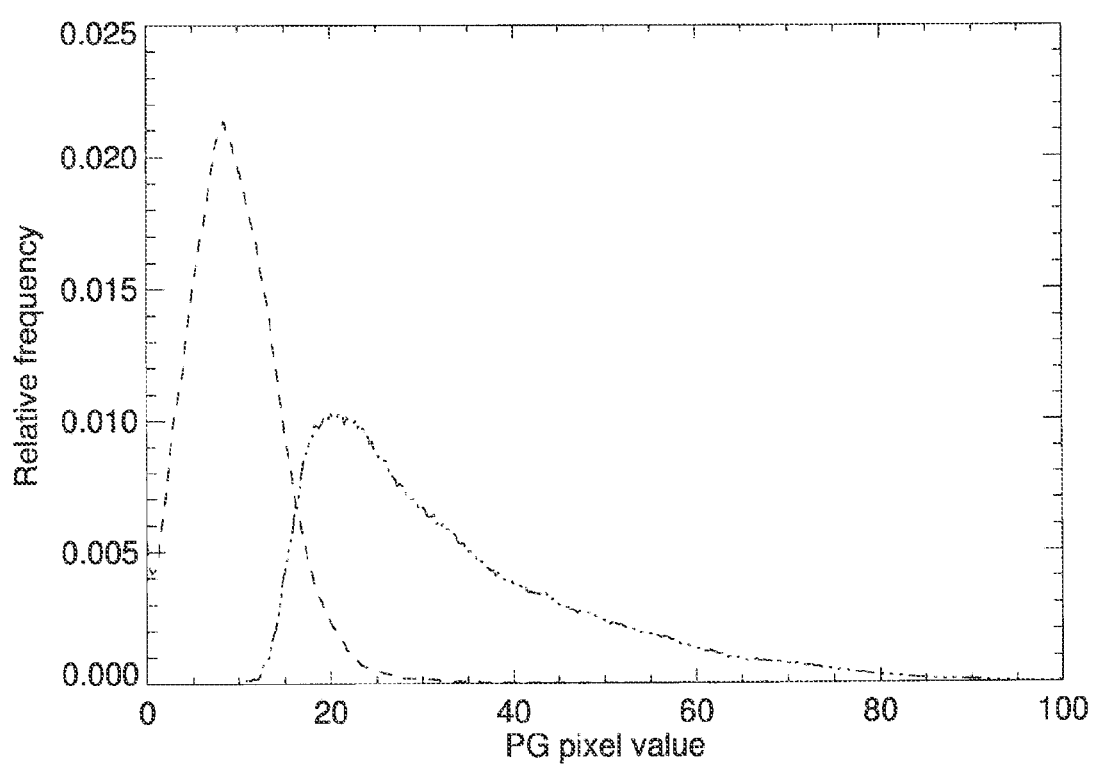
FIG. 8 is a graph illustrating glandular and adipose percent glandular ensemble probability density functions from the first example study.

To explain the correlation and relationships between three breast density measures, the empirical distributions were derived from the expanded dataset for the adipose and glandular tissue types, which are shown in FIG. 8. Referring to FIG. 8, the graph shows the adipose (dash) and fibro-glandular (dot) empirical ensemble probability distribution function approximations derived from the expanded dataset. These are the component distributions used for the mixed distribution model. These represent a summary of the entire dataset and they show that the total collection of PG representation images can be decomposed into two single-mode distributions. These were constructed by first generating the $PD_c$ labeled images. For the $PD_c$ measure, Az=0.69 (for the cancer-side dataset adjusted for BMI and breast area), which indicates the validity of the method used to form these component distributions (FIG. 8). These distributions were used to evaluate the Eq. (4) expression relating the three breast density measures by estimating their (the distributions) respective means and standard deviations giving: $(m_1, m_2)$= (32.3, 9.7) and $(\sigma_1, \sigma_2)$=(14.6, 4.9). The mixture coefficient c [see Eq. (3) and Eq. (4)] was derived from each image as the breast density measure (approximation for PD) to assess the Eq. (4) approximation. The c measure quartile associations with breast cancer (cancer side dataset) and Az were similar to that of PD (FIG. 3) when adjusting for breast area and BMI [odds ratios: 1.0 (ref.), 2.6, 3.5, and 5.5, and Az=0.67]. Although Eq. (4) shows the connection between the various measures, understanding the positive correlation between m and σ, theoretically, requires manipulation. $c_s$ (simulated c variable) was generated over this range (0,1), Eqs. (3-4) were generated as functions of $c_s$ using the density quantities ($m_1$, $m_2$, $\sigma_1$, $\sigma_2$), and it was found that the theoretical linear correlation between PG and $PG_{sd}$ [i.e., correlation between Eq. (3) and square root of Eq. (4)], which gave $R_T$=0.79. This theoretical correlation is in agreement with the measured correlation between the PG and $PG_{sd}$ shown in FIG. 5 (last column). As Eq. (4) shows, $PG_{sd}$ is a positive valued function of increasing c but it is not monotonic.

Discussion

The analysis resulted in three important findings. First, the $PG_{sd}$ measure showed greater magnitude of association with breast cancer than the other measures in a side-by-side comparison. In contrast, the calibrated PG measure was the least associated breast density measure, which agrees with other calibration investigations. Secondly, the work provides evidence for the correlation between the measures. Connecting the image variation ($PG_{sd}$ measure) with the normalized PG representation, PG measure, and the PD measure with the mixed distribution relationship is an important contribution to breast density research. This relationship shows that the three measures are characterizing different attributes of the same phenomenon and helps to explain the positive correlation between the measures. Previous work showed that the calibrated PG measure can be used to explain the information captured by the PD measure. These earlier findings were reinforced by the mixed distribution formulism. There is also another condition that may contribute to the positive correlation. Although most likely non-parametric, these distributions (FIG. 8) individually exhibit skewed right tail behavior similar to that of Poisson, low-order central Chi-square, and more generally lower order gamma probability density functions for example. In these non-symmetric parametric densities, the mean and standard deviations are functions of the same parameters, implying they are related (often termed signal dependent noise). By hypothesis, the findings suggest that PD is an approximation for the $PG_{sd}$ measure. Thirdly, the work showed that breast area may be a confounding factor for both calibrated measurements as well as for the PD measure.

The $PG_{sd}$ measure magnitude of association is consistent with previous work that found low frequency Fourier features show association with breast cancer similar to that of PD. Because the mammograms have approximately a $1/f^\beta$ power spectrum, the majority of the image pixel intensity variation is captured in the lower frequency portion of its Fourier power spectrum. Although the power spectrum of the calibrated FFDM images used in this report were not investigated here, the previous spectral analysis of similarly acquired FFDM images holds in general for these calibrated images. For a given target/filter calibration and fixed x-ray tube voltage, the calibration mapping is linear; this linear mapping preserves the spectral functional form within a constant and scaling factor. Thus for a given calibrated image, the measured $PG_{sd}$ quantity is heavily influenced by the low frequency portion of its power spectrum. This relationship is also consistent with (and applies to) the standard deviation measure estimated from the raw data.

Both the choice of dataset and breast area influenced the findings. Previous work showed that choosing the cancer-side or non-cancer side breast was of little consequence in the association analyses for the PD measure. At this time, it is not clear if this relation holds for the $PG_{sd}$ measure. It was found that the $PG_{sd}$ measure is more predictive in the cancer-side dataset in comparison with non-cancer-side dataset. However, the same relationship held for the PD measurements as well. Previous work showed that the left breast has a tendency to be larger than the right breast and this asymmetry is exaggerated in women with breast cancer, but these asymmetries do not explain the differences noted here in the case-control breast areas. The mammography type-unit used for this work was the first FDA approved FFDM unit in the US. This system has a smaller detector than newer FFDM systems and has a problem accommodating larger breasts in a single acquisition. In multiple-mammography unit facilities that have mixed detector sizes, x-ray technicians (as ascertained from technicians at this center) direct women with larger breasts (by observation) to units with larger detectors. All of the control image samples were derived from images acquired with this selection process for this FFDM unit under normal screening conditions. In contrast, a portion of our cancer cases was recruited and imaged without regard to this selection process indicating that their projected breast areas may be greater than those of the controls. The breast area distribution summaries (FIG. 2) show this holds. The findings for the reduced dataset indicated that this bias has negligible influences when controlled for it in the full dataset analysis. The findings indicate that controlling for breast area is as important as controlling for BMI when investigating measures of breast density. Evidence also indicates larger breasts tend to have less breast density as reviewed by these researchers, which agrees with the overall negative breast density measurement correlation with breast area relation found here.

At this time, both forms of the variation measure (standard deviation) appear to viable breast density measures. Both forms are automated. The raw image measure does not require the development of a calibration platform, representing considerable research effort reduction. The measure derived from the calibrated images has the benefit of being strictly defined with a specific data representation. For example, the mixed distribution formulism was only possible via the calibration application.

Second Example Study—Comparison of Calibrated and Non-Calibrated Measurements

Methods

Methods: Study Population

The patient accrual was part of an ongoing case-control study. The study population, selection methods, and matching particulars have been discussed previously and are not discussed here in detail. In brief, the study accrual has been updated in this example study to include more participants. In this IRB approved study, women diagnosed with a primary breast cancer (September 2007-March 2011) were included as cases (n=160) identified from those attending the breast clinics at the H. Lee Moffitt Cancer Center. For the controls, three groups of cases were considered based on their screening history. Group 1 was comprised of women that had a negative screening mammogram within 30 months prior to their breast cancer diagnosis (n1=141). Group 2 was comprised of women who had a negative screening history that fell outside of the group 1 parameters, such as a woman who had a screening in 2007 but not again until 2010 at which time she was diagnosed with cancer (n2=14). Group 3 was comprised of women who were just starting screening and were diagnosed at their baseline mammogram (n3=5). Case data and images were either located by retrospective records review (n=52) for those women with images archived on the study $FFD_M$ unit or recruited, consented, and imaged for the study (n=108). Controls (n=160) were identified retrospectively from the pool of women undergoing breast cancer screening mammography at the H. Lee Moffitt Cancer Center with archived images acquired with the study FFDM unit and were matched (individual) to their cases by age (±2 years) and hormone replacement therapy usage and duration (±1 year).

Methods: Spatial Variation Breast Density

Figures 10, 11:
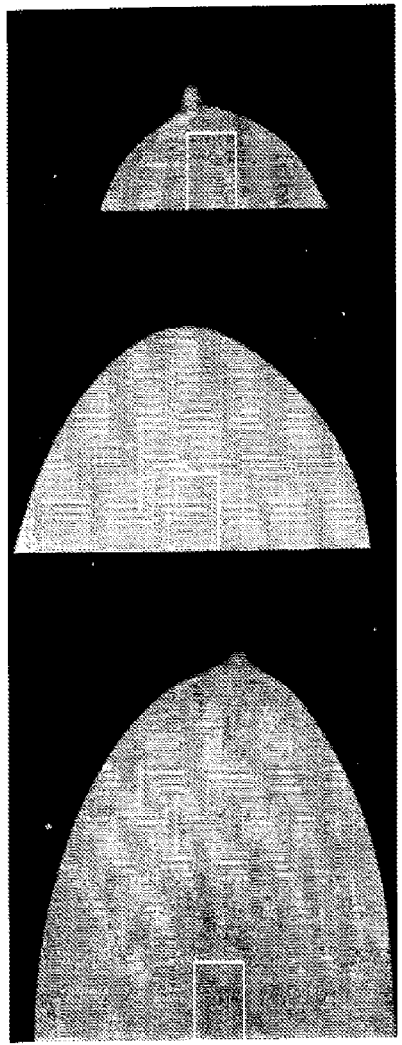
FIG. 10 illustrates additional example images created by a study FFDM unit used as raw image surrogates for display purposes only.
FIG. 11 is a table of patient characteristics from a second example study.

Various breast density measures and their association with breast cancer were compared using a matched case-control design. To reduce anomalous spatial variation, the analysis was contained to the portion of the image that was in contact with the compression paddle during imaging. For example, as discussed above with reference to the first example study, the breast image area was eroded by 25% along a radial direction. This area defined the effective breast area. The degree of breast area reduction is an approximation that eliminates anomalous region where the compressed breast thickness is not well defined. Both $PG_{SD}$ and the standard deviation calculated from the raw data (or $R_{SD}$) were derived from this modified breast area. The measures $R_{SDL}$ and raw image standard deviation from the fixed box ($R_{SDX}$) were derived from reducing the effective breast area further and calculating the standard deviation. The raw image standard deviation from the reduced breast area ($R_{SDL}$) was derived with 35% erosion. Because mammograms have a fractal characteristic, $R_{SDX}$ was considered by restricting the measure to a 3×3 cm² box within each image. The box was located by first segmenting the breast region from the background and forming a binary mask, where the breast region pixels were set to one (1)

and the other pixels were set to zero (0). Parallel to the chest wall, the box was centered on the centroid (determined with the binary segmented image) and extended from the detector edge to 3 cm along the direction perpendicular to the chest. Examples of the box location-size are shown in FIG. 10, which illustrates additional example images created by a study FFDM unit used as raw image surrogates for display purposes only. Referring to FIG. 10, from left to right, the image with the largest box area/breast area ratio, the image with the medium ratio, and the image with the smallest ratio (right) are shown. The image areas from left to right in pixel units are 2,426,894, 1,324,519 and 386,023. The outlined box is 3×3 cm$^2$ (300×300 pixels) and is vertically centered on the segmented image vertical centroid coordinate. The raw image standard deviation from the fixed box ($R_{SDX}$) breast density was derived from this region. These images are processed clinical display images. This measure was used to investigate (or control for) two possible influences. First, in fractal noise fields such as mammograms, the variance is a function of the region-size from which it is measured, where the larger the area, the larger the variance. Second, $PG_{SD}$ is a decreasing function of increasing breast area. All measures of breast density were compared with PD as means of standardized control.

Methods: Percentage of Breast Density (PD)

The dataset consisting of all cases-control images (left and right CC view images) were first de-identified and randomized. PD was generated with the Cumulus3 (CM) software (University of Toronto) using the batch file procedure to process the raw (non-processed images) FFDM images. The CM operator was blinded to the case-control status and original image identifiers. To avoid operator fatigue, a single operator performed the PD labeling in multiple reading sessions.

Methods: Breast Cancer Association Comparisons

To assess the breast density measure association with breast cancer, the non-cancer breast of each case was matched with the ipsilateral breast of its control. All mammograms were performed with a General Electric (Milwaukee, Wis.) Senographe 2000D FFDM mammography unit (i.e., one unit) that is used for routine screening at our center. The Craniocaudal (CC) views were used for all our analyses. A standard quartile analysis with conditional logistic regression was used for the odds ratio (OR) comparisons, where the control breast density distribution was used to determine the cutoff values for each measure. The first quartile of breast density for each measure served as the reference group for the second to fourth quartiles, providing a means for comparing the intermeasure OR distributions. Body mass index (BMI) measured in kg/m$^2$ and breast area (pixel units) were used as continuous variable adjustments in the analyses, whereas menopausal status was adjusted as a binary variable. The area under the receiver operating characteristic curve (or Az) was also used for predictive capability comparisons. This analysis (including the Az estimations) was performed with the SAS software package (SAS Institute Inc., Cary, N.C.).

Methods: Calibration Assessment

An objective of this work was to investigate the nature of the calibration without considering the case-control status as the end point comparison. Similar pixel distribution measures were derived from calibrated and non-calibrated mammograms and compared. The average (or PG) and standard deviation of the calibrated pixels values (i.e., $PG_{SD}$) were used as the two calibrated measures. The mean ($R_M$) and standard deviation (i.e., $R_{SD}$) of the raw pixel values were used as two non-calibrated measures. The respective means and standard deviations were investigated with linear regression analysis. For this analysis, we used the combined image dataset (i.e., 320 study images derived from both cases and controls).

Results

Results: Breast Density Measurement Association

Demographic and risk factor distributions are presented for both breast cancer cases and controls in FIG. 11. Referring to FIG. 11, the table provides the number (n) of cases and controls in the hormone replacement therapy (HRT) stratifications by years and for the other measures. The mean and standard deviation (SD) for the age, body mass index (BMI), breast area distributions, and menopausal status (postmenopausal or not) breakdown by case-control group are also provided. Note, BMI was missing for one case observation. However, the cases have a few more menopausal women and the majority of women overall all postmenopausal.

Associations between the five breast density measurements and breast cancer are summarized in FIG. 12. Referring to FIG. 12, the quartile odds ratio (OR) stratifications and area under the receiver operating characteristic curve (Az) quantities for each of the five breast density measures: 1) operator-assisted percentage of breast density (PD), 2) calibrated standard deviation ($PG_{SD}$), 3) raw image standard deviation ($R_{SD}$), 4) raw image standard deviation from the reduced breast area ($R_{SDL}$), and 5) raw image standard deviation from the fixed box ($R_{SDX}$) are shown. The number of cases in each stratification (n1-n4) is listed in the top row. 95% confidence intervals (CIs) are provided parenthetically next to each OR. In the analysis, body mass (BMI), breast area (area), and menopausal status were controlled. The two groups are similar in most measures. In FIG. 12, the ORs and Az quantities were adjusted for BMI, simultaneous adjustments for BMI and breast area, and the simultaneous adjustments for all three factors. When controlling for all factors, $PG_{SD}$ provided the largest OR associations with breast cancer (OR: 1.0 [ref.], 4.6, 4.3, 7.4; Az=0.651) among the measures. In comparison, the PD associations (OR: 1.0 [ref.], 2.7, 2.9, 5.2; Az=0.643) were somewhat diminished. The $R_{SDL}$ associations (OR: 1.0 [ref.], 2.9, 4.4, 5.4; Az=0.654) were slightly greater than PD, and the $R_{SDX}$ associations (OR: 1.0 [ref.], 3.5, 3.1, 4.9; Az=0.650) were similar to PD. In comparison with the other measures, $R_{SD}$ provided the weakest association (OR: 1.0 [ref.], 2.2, 2.9, 3.8; Az=0.634). The estimated standard error (SE) for all Az quantities was $SE_{Az}$~0.03 indicating the inter-measure Az differences are marginal for most comparisons. To help explain the $R_{SD}$ and $R_{SDL}$ relative association, the calibrated standard deviation calculated from the 35% eroded breast region (or $PG_{SDL}$) was investigated. In contrast, the $PG_{SDL}$ associations weakened when using the reduced breast area but were similar to that of PD (data not shown).

Figure 13:
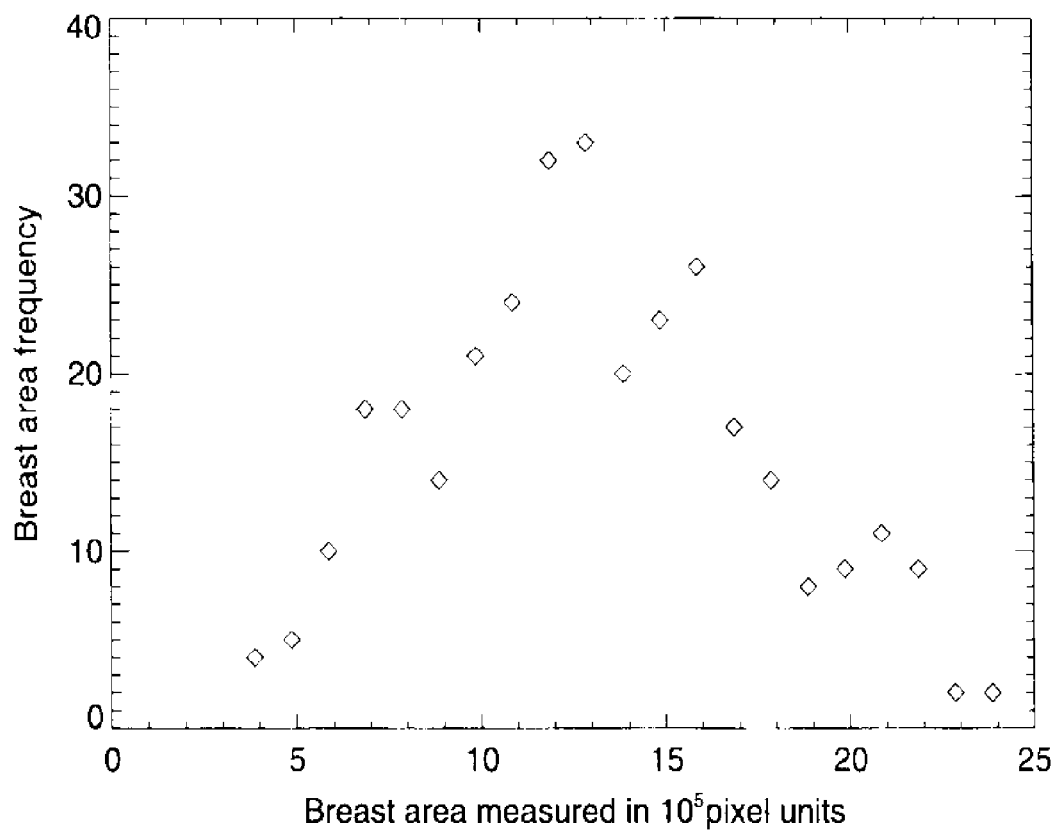
FIG. 13 is a graph illustrating the breast area histogram from the second example study.

To estimate the area loss resulting from the erosion process, a coarse approximation that applies to CC views was used. Assuming the breast area (A) geometry is a half-hemisphere, A~$r^2$, where r is the radius, the differential area change approximation with respect to the erosion is given by dA~2R×ΔR, with ΔR=0.25×R or 0.35×R for the 25% and 35% erosion, respectively. The percentage area reduction is then ~100%×dA/A, which gives 50% and 70%, for the 25% and 35% erosion. Thus, the $R_{SDL}$ measure included roughly 30% of the available pixels within the breast region, whereas $R_{SD}$ included 50% of the pixels. To put the $R_{SDX}$ measurement in context, the box relative to various breast sizes is shown in FIG. 10. From left to right, the box relative to the larger breast, medium size breast, and smallest breast in the dataset are shown in FIG. 10. The breast area histogram is shown in FIG. 13. Referring to FIG. 13, the frequency histogram for the breast area measured in $10^5$ pixel units (i.e., the bin-width used for the horizontal axis). The symmetric behavior indicates most images are similar to the middle image in FIG. 10. The symmetric behavior (and central tendency) shown in FIG. 13 indicates that many of the images have breast areas similar to the medium size breast shown in FIG. 10 (middle illustration). For all measures, the ORs and Az quantities increased (increased magnitude of association) when controlling for (a) BMI, (b) BMI and breast area, and (c) BMI, breast area, and menopausal status. However, the four variation measures were more strongly influenced by the breast area than PD when considering the respective ORs. The ORs for the box-restricted measure were also influenced by breast area. These findings also indicate that menopausal status is captured by the breast density measures to varying degrees. For example, we let $x_0$=the 4th quartile OR without controlling for menopausal status and $x_1$=4th quartile OR when controlling for menopausal status for a given measure. The percent change (PC) is then given by PC=$(x_1-x_0)/x_0 \times 100\%$. For the calibrated $PG_{SD}$, PC=20.2%, and for the $R_{SDL}$, PC=8.7%. In contrast, for PD, PC=1.4% and for $R_{SDX}$, PC=2.7%. Because the calibrated measure was influenced the most by menopausal status, its relationship is further assessed. $PG_{SD}$ was used to predict premenopausal status with logistic regression, which gave OR=1.9 (1.5-2.5) per standard deviation change in $PG_{SD}$ and Az=0.690.

Figure 14:
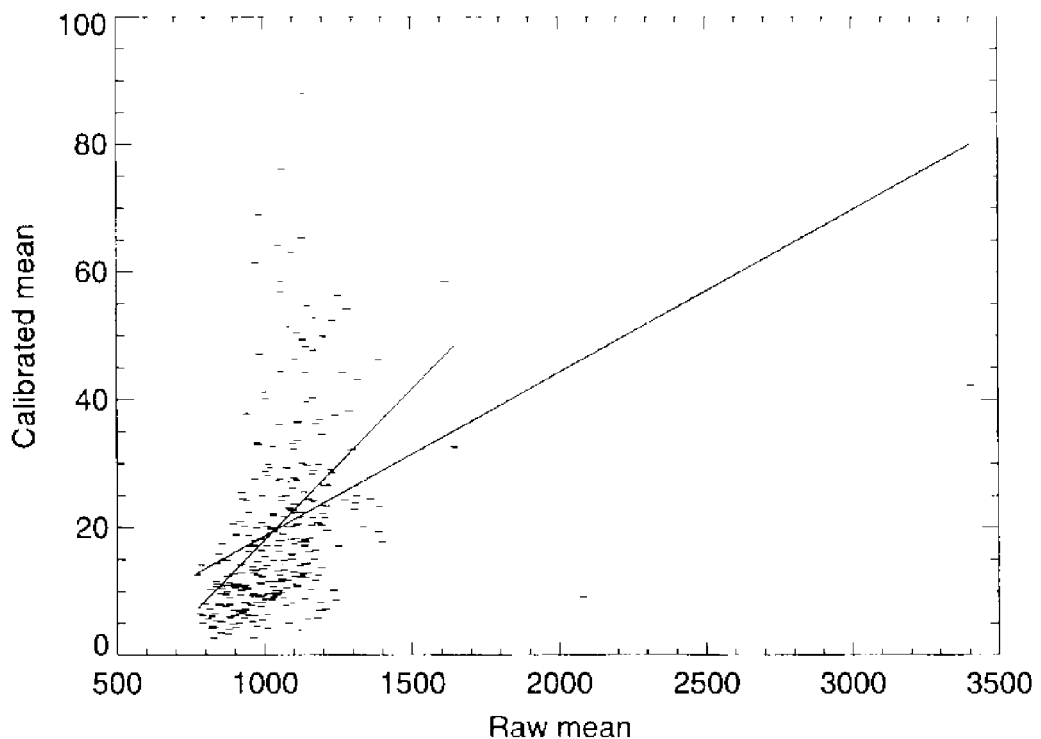
FIG. 14 is a graph illustrating the percent glandular breast density measure and the raw image mean value regression analysis from the second example study.
Figure 15:
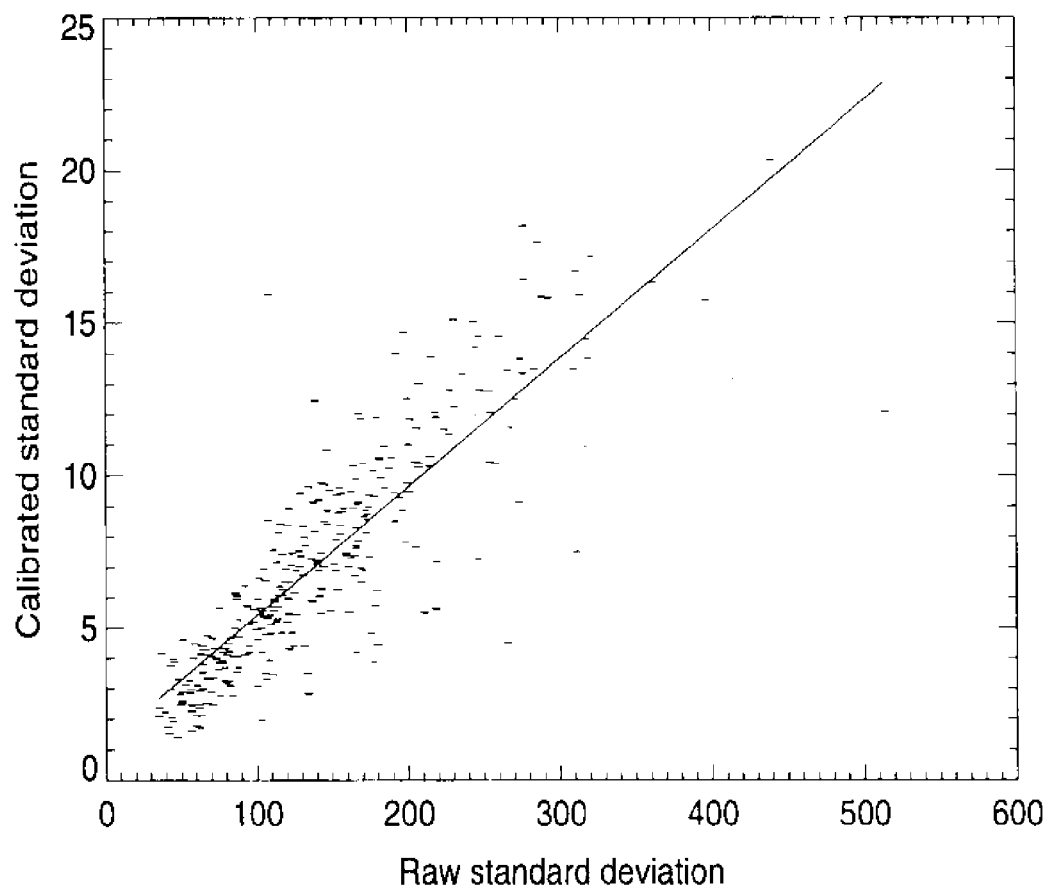
FIG. 15 is a graph illustrating the percent glandular standard deviation breast density measure and the raw image mean value regression analysis from the second example study.

Results: Correlation Comparisons To show the influence that the calibration has on the raw image mean (or $R_M$), the calibrated mean (or PG) was modeled as a linear function of $R_M$ (FIG. 14). Referring to FIG. 14, the calibrated mean values modeled as a linear function of the raw image mean values (dashes) are shown. The regression-fitted lines (solid) show the two measures are not described well by this relationship, indicating the calibration has a strong influence. The data were modeled with all the points (line with the longer length) and with three outliers removed (line with the shorter length) from the right. The respective slope (m) and standard errors for each plot were m=0.026±0.004 and 0.047±0.005 with $r^2$=0.12 and 0.19. In this plot, the entire dataset (the line with greater length) and a restricted dataset determined by removing three outliers located to the right (the line with shorter length) were used. The respective slopes for each line were m=0.026 (SE=0.004) and 0.047 (SE=0.005). In both cases, the slopes were significantly different from zero (P<0.0001). However, the respective coefficients of determination were $R^2$=0.12 and 0.19, indicating the linear model does not explain the relationships well. Referring to FIG. 15, the calibrated standard deviation modeled as a linear function of the raw image standard deviation (dashes) is shown. The slope and standard error were m=0.042±0.002. The regression fitted line (solid) shows the two measures are highly correlated ($R^2$=0.73) indicating that the calibration re-scales the standard deviation quantities while approximately maintains the internal distances between the samples. As shown in FIG. 15, $PG_{SD}$ (calibrated standard deviation) was modeled as a linear function of $R_{SD}$ (the raw image standard deviation), which gave m=0.042 (SE=0.002 and P<0.0001) with $R^2$=0.73. Because of the $R_{SL}$ significant OR associations, a similar regression was performed with $PG_{SL}$, which gave m=0.048 (SE=0.001, P<0.0001) and $R^2$=0.77 (plot not shown). Thus, the standard deviation measures derived from the two different data representations are collinear.

Discussion

The second example study investigated various automated methods of measuring breast density and made comparisons with PD. All measures of breast density showed a significant association with breast cancer to varying degrees. Among the measures, $PG_{SD}$ showed the strongest OR associations with breast cancer, indicating calibration produced information not retrievable or available from the raw data representation. Furthermore, the relationship between PG and $R_M$ was not described well by a linear model. In contrast, the linear model reasonably explained the relationship between the $PG_{SD}$ and $R_{SD}$ measures. This provided supporting evidence for the significant association produced by the raw image breast density measures. These findings suggest that much of the data within the breast area confound the standard deviation measures from the raw data. $R_{SDL}$ was based on the analysis of roughly 30% of the breast area, whereas producing significant associations. Eliminating a significant portion of the breast region improved the raw image standard deviation associations, whereas further erosion diminished the $PG_{SD}$ associations. The $R_{SDX}$ findings are more difficult to interpret. This measure produced significant association while considering a relatively small section of the image in many situations. Moreover, the OR relationships were influenced by controlling for breast area. Possible reasons for the elevated associations may be that this box region is likely to include the focal spot and the distance between the compression paddle and detector is relatively more uniform in comparison with larger regions. The second example study also showed that standard deviation measures were more heavily influenced by both menopausal status and breast area in comparison with PD. The relationships with menopausal status, breast area, and the new breast density measures will require further analyses to fully understand the underlying mechanisms.

Conclusions

The calibrated measure provided the strongest OR associations among the measures considered. The standard deviation measures from the raw mammograms also provided significant associations with similar predictive capability as the calibrated measure (i.e., the Az findings). Both the calibrated and non-calibrated variation measures are automated. The gains from calibration result from considerable phantom imaging and data analyses, which are required to maintain calibration accuracy. In contrast, $R_{SDL}$ results from a relatively simple algorithm.

Both standardization and automation of breast density reporting would assist the radiologist in providing a further measure of risk to the referring clinician and provide a means for developing personalized screening frequency strategies. Realization of this potential is based on an algorithm to accurately and reliably quantify breast density independent of a subjective reader and in a manner that does not disrupt clinic throughput or patient management. These new measures may provide automated solutions for the measurement of breast density after undergoing rigorous evaluations with different datasets.

Third Example Study—Automated Mammographic Density Methods

Methods: Study Population

Data from three studies at the Mayo Clinic were used in this research effort and are described below. All three studies were approved by the Mayo Clinic Institutional Review Board. Mayo Mammography Health Study (MMHS) is an ongoing cohort study of female residents of Minnesota, Wisconsin and Iowa over the age of 35, having screening mammography at the Mayo Clinic between 2003 and 2006, and with no personal history of breast cancer. Participants completed a questionnaire, provided consent to mammograms, medical record and linkage to state cancer registries. The 19,924 participants (response rate, 51%) are followed for incident cancer events through the tri-state cancer and Mayo Clinic tumor registries.

The current analysis is based on follow-up through December, 2008 and includes 231 incident and histologically confirmed primary breast cancers; fifty nine cases diagnosed within 60 days of the enrollment mammogram were excluded. A case-cohort design was used to efficiently target mammogram collection efforts to a random sample or subcohort of 2300 women from the entire MMHS cohort as well as all incident breast cancers. Excluding women with digital mammography, a total of 217 cases and 2094 subcohort members were available for analyses.

Mayo Clinic Breast Cancer Study (MCBCS) is an ongoing clinic-based breast cancer case-control study initiated in February 2001 at Mayo Clinic, Rochester, Minn., described previously. Cases are recruited within six months of date of diagnosis from a six state Midwestern region. Controls without prior history of cancer are recruited from the internal medicine practices at Mayo Clinic and frequency matched to cases on age (5-year age category), race and state of residence. Analyses are based on 1870 cases and 1628 controls enrolled through October, 2008 with 69% case and 71% control participation. Mammograms were available and digitized for 940 (50%) cases and 1087 (65%) controls.

Mayo Clinic Mammography Study (MCMAM) is a matched breast cancer case-control study nested within the mammography screening practice in Rochester, Minn. Cases (n=373) and controls (n=713) were 50 years or older, lived within a 120 mile radius of Rochester, and required to have at least two screening mammograms prior to diagnosis (cases) or referent date (controls). Controls without breast cancer were matched to each case on age (within 5 years), screening exam date (4 months), menopausal status, interval between mammograms (8 months), prior screening mammograms (1 mammogram) and residence (county). Based on the need to digitize films at a higher resolution, mammograms were only available on 246 cases and 522 controls.

Mammogram Retrieval, Digitization and Percent Density Estimation

The earliest available mammogram before diagnosis (or enrollment date) was used for primary analyses. For MMHS and MCMAM, there were 4.7 years and 3.7 years on average between mammogram and diagnosis (or enrollment) date. This interval was shorter (22 days) in MCBCS, since the majority of cases only had films available at date of diagnosis. Mammograms of the contralateral (for cases) or left (for controls) breast were digitized. For secondary analyses that evaluated the influence of acquisition parameters on the PD and V associations with breast cancer, the enrollment mammograms in the MMHS case-cohort were used, since the earlier mammograms above did not have this information readily printed on the image. All mammograms from MMHS and the majority from MCBCS (80%) were digitized on the Array 2905 laser digitizer (Array Corporation, Netherlands) that has 50 micrometer (limiting) pixel spacing with 12-bit grayscale bit depth. Mammograms from the MCMAM study and 20% of MCBCS were digitized on a Kodak Lumiscan 85 scanner at that has 50 micron (limiting) resolution with 12-bit grayscale depth (Eastman Kodak Co, Rochester, N.Y., USA)).

Percent Mammographic Density (PD) Measure

PD was estimated from the Craniocaudal (CC) mammogram view in all three studies by the same expert reader. PD (dense area divided by total area×100%) was estimated for each view using a computer-assisted thresholding program, i.e., Cumulus discussed above. Briefly, two thresholds are set; one separates the breast from the background and the second separates dense from non-dense tissue. For these studies, high reliability was demonstrated (r(correlation)>0.93 for all studies) while reading over 1500 duplicate images across varying time frames.

Percent Glandular Standard Deviation Measure

The V algorithm is comprised of two steps. First, the breast area is segmented from the background automatically to remove image artifacts and detect the breast area, as discussed above. This produces a binary mask image that is used as an overlay for the corresponding original image to constrain the processing to a specific region. The marked breast area is used in the second step. This binary half-moon silhouette image is then eroded by 25%, for example, as described previously. However, as discussed above, the percentage of erosion is not limited to 25%, and may be in the range of 0-35%, or any other percentage range. This leaves the region where the compressed breast thickness is approximated as uniform and removes those that could potentially interfere with the measure. The V measure is the standard deviation of the pixel values within the eroded breast region for each study image. All mammograms were processed with the same algorithm.

Acquisition Parameters

To evaluate the potential influence of the image acquisition technique on the V and PD-breast cancer associations, the values for the compressed breast thickness, compression force, x-ray tube voltage, and beam current-time as a surrogate for the x-ray generation, were abstracted from mammograms digitized at enrollment from the MMHS case-cohort.

Statistical Methods

Data were summarized for each study by case and control (or subcohort) status. Associations between the V measure and PD were visualized using scatter plots and Spearman correlation coefficients, with 95% confidence intervals (CIs), summarized the strength of the linear association between the two measures. Ordinal tests of trend were performed to assess the association between each density measure and breast cancer risk. The magnitude of the associations were estimated using odds ratios (ORs) or hazards ratios (HRs) reflecting the relative risk of breast cancer for a woman whose measurement was one standard deviation higher than that of another woman or for quartiles of V or PD. For the case-cohort study (MMHS), HRs were estimated using Cox proportional hazards regression using sampling weights to account for the subsampling that was performed in this case-cohort design. For the case-control studies (MCBCS and MCMAM), ORs were estimated using logistic regression.

A meta analysis was also performed using a random study effect to obtain across-study pooled estimates. To combine the study-specific estimates, ORs from the case-control studies were transformed to approximate relative risks. The delta method was applied to obtain approximate standard errors of these log-transformed relative risks.

To compare the ability of the two measures to identify women at greatest risk of breast cancer, the area under the receiver operator characteristic curve (AUC), or concordance statistic, was estimated. This statistic can be estimated as the proportion of case-control pairs where the risk factor predicts the case to have a higher risk than the control. Values of 0.5 suggest that the risk factor(s) cannot discriminate between cases and controls, and values of 1.0 suggest that the model provides perfect discrimination.

Tests of association between density measures and breast cancer while adjusting for image acquisition were performed. In order to determine the effect of acquisition parameters on the observed associations, the degree to which the relative risk and AUC estimates were affected by their inclusion as covariates were examined.

All analyses controlled for age at mammogram, BMI and menopausal status. Tests of significance were two-sided and analyses were performed using SAS statistical software (SAS Institute Inc., Cary, N.C.).
Results Participant characteristics are summarized in FIG. 16 by study population. The MCMAM study was mostly postmenopausal (91%), and had the highest average age (64.9 years for cases and 64.1 years for controls) while the MMHS study had the largest number of premenopausal cases and controls (43-54%), reflected in the youngest mean ages (55.4 and 51.6 years, respectively). BMI was comparable across all populations. Average percent density and V were higher in cases compared to controls.

Figure 19A:
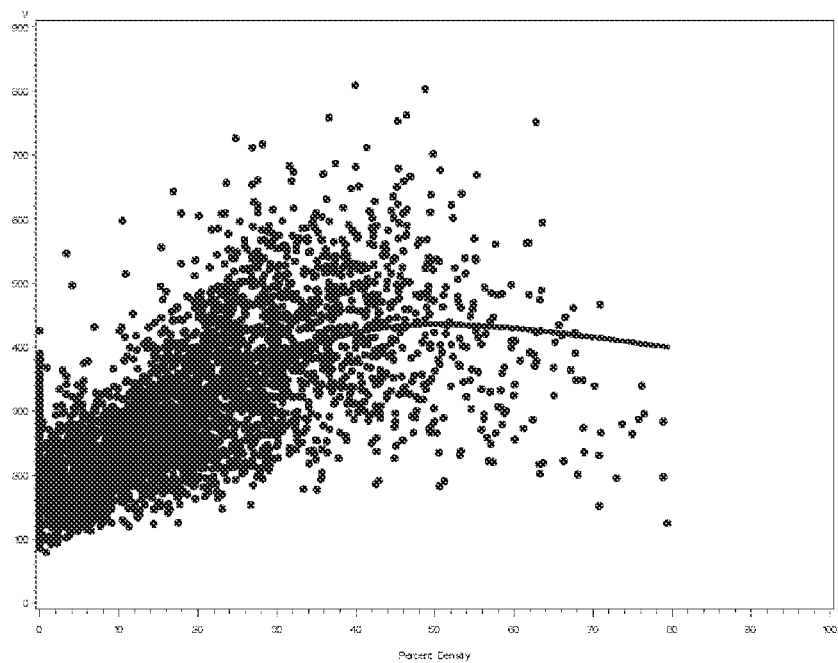
FIGS. 19A and 19B are graphs illustrating an association between the percent glandular standard deviation breast density measure and the percent density measure.
Figure 19B:
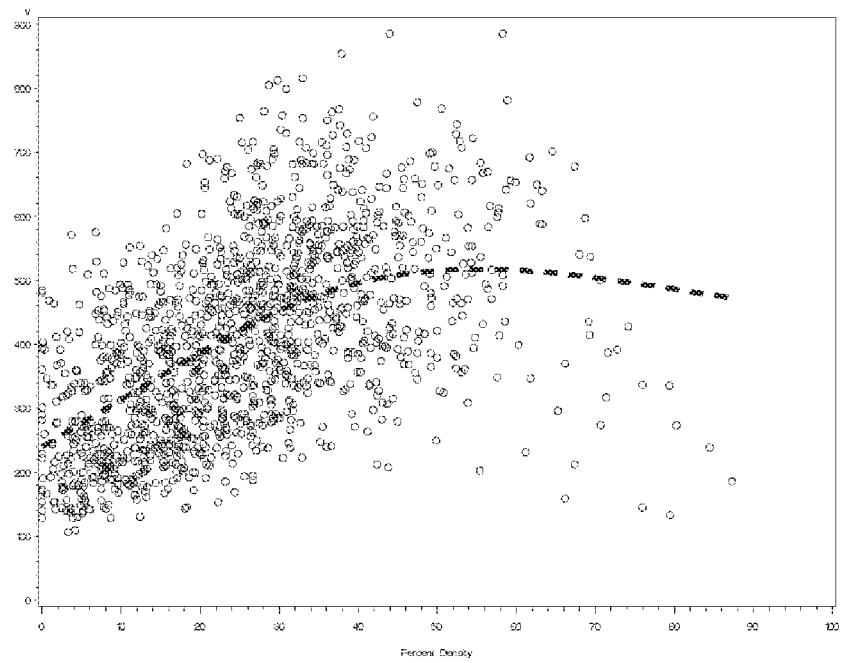

FIGS. 19A and 19B illustrate that the V and PD density measures are moderately correlated, with an $R^2=0.64$ for all studies combined ($R^2$ ranges from 0.64-0.66 for individual studies). This association is linear only at low to moderate percent densities (<40%). The associations between both density measures with BMI, age, and menopausal status are shown in FIG. 16. Both V and PD were highest in premenopausal, younger women and those with low BMI.

All three studies reveal positive associations between the V measure and breast cancer (FIG. 17). Within the 217 cases and 2094 subcohort of MMHS, V was associated with breast cancer [HR for increasing quartiles: 1.0 (ref.), 0.9, 2.1, 7.0, p-trend<0.001]. The corresponding findings for PD were attenuated in the top two quartiles, by comparison [HRs: 1.0 (ref.), 1.5, 1.6, and 3.1, p-trend<0.001]. Positive associations between V and breast cancer were also seen in the 928 cases and 1039 controls from MCBCS [OR: 1.0 (ref.). 1.3, 3.0, 10.7, p-trend<0.001], with slightly higher estimates in the top quartiles compared to PD [ORs: 1.0 (ref.), 1.6, 2.0, and 4.4, p-trend<0.001]. Importantly, these two studies show greater discriminatory accuracy for the V-breast cancer (AUC=0.71 and 0.76) compared to PD-breast cancer (AUC=0.64 and 0.65) association. The MCMAM study of 246 cases and 515 controls showed similar associations and AUC (0.60 vs. 0.61) for both V and PD (FIG. 17).

The meta-analysis of the three studies showed positive associations of breast cancer with both V (RR=1.0, 1.3, 1.9, 3.5) and PD (RR=1.00, 1.3, 1.5, 2.2).

The third example study was interested in whether the V-association remained when examining mammograms at least 2 years prior to the cancer, since this would be important for eventual risk prediction. Only the MMHS and MCMAM studies were used for these analyses due to the timing of mammogram films. In both studies, there were essentially no differences by timing of mammogram in respect to the breast cancer (<2 years vs. >2 years) [Data not shown].

The third example study also assessed the influence of inter-patient acquisition parameters on the density associations within the MMHS study. FIG. 17 shows that adjustment for these factors had little influence on the association between either PD or V and breast cancer.
Discussion An automated estimate of mammographic density (the V-measure) is a risk factor for breast cancer in three epidemiologic studies. In two studies, the V association was stronger than PD, reflected in greater magnitude of risk estimates for the highest two quartiles and greater discriminatory accuracy. The V-breast cancer association was not materially influenced by acquisition parameters, and this association was similar to that seen in the initial study of a calibrated V measure and breast cancer using digital mammography or FFDM. Taken together, the V measure may be a viable automated mammographic density measure that is consistent across film and digital platforms and has potential for translation to the clinical setting for risk estimations.

Several of the findings support the V measure being incorporated into future risk models. First, the V-breast cancer association remains strong when assessed on mammograms at least two years prior to diagnosis. Second, V can be measured from FFDM, the primary screening modality in the US, and the association is similar to film mammograms. Thus, V appears to be an important risk assessment tool across imaging platforms. Next, the V measure provides better discrimination of breast cancer cases vs. controls in two of the three studies. And, the magnitude of the AUC for these two studies (including age, BMI and menopause) was 0.70 or above, which is higher than that seen with the current Gail model (C-index of 0.596) and breast cancer risk models incorporating PD estimates to date, with ranges of C-index from 0.

Although these studies showed V to perform as well as PD in discrimination of risk, there was heterogeneity in results. The MCBCS and MMHS studies showed improved discrimination of risk and increased relative risk estimates for the upper quartiles while the MCMAM study found essentially similar results. The reason for this heterogeneity is not clear. The influence of several factors on the V-association across all studies including age, menopausal status, mammogram time period, type of digitizer, and type of cancer (invasive vs. in situ) cancers was examined, but no explanation for these differences between studies was found. One aspect that could contribute to differences in discrimination was that MCMAM was a closely matched case-control study; there is the potential that we overmatched on some factor related to the V measure. Thus, that the V-measure performed as well as PD in all three studies, but whether the V-measure is superior to PD requires additional research.

Mammographic density has been studied for many years, most often assessed as the amount or proportion of bright tissue in a given image. Thus, a plausible case must be made as to why a measure of variation (V) of this tissue is relevant to breast cancer when it doesn't represent the actual amount or proportion. Evidence supporting the V measure can be distilled from recent calibration work and from past texture analyses. First, the calibrated V in FFDM was found to be a function of the PD measure. Secondly, the V measure includes both the low frequency features and fractal texture measures that were investigated previously and found to influence breast cancer. Thirdly, the V measure as well as the texture measures are related to one of the earliest density measures, the Wolfe parenchymal pattern, which has been strongly associated with risk of breast cancer. This early work was formulated by noting the variation in mammograms was related to risk. Thus, the new V measure indirectly correlates with percent density measures in the past, but the third example study presents the first direct assessment of this measure with breast cancer.

Strengths of this study include the validation of a novel breast density measure across three well designed epidemiology studies. The V-association was comparable to the PD-association, and in two of three studies resulted in improved risk discrimination, AUCs >0.70. V is automated and generated without thresholds or other detection related parameters. As noted previously, the V can be measured in both film and FFDM, and the corresponding associations have now been shown to be similar.

In the study, there was limited follow-up in MCBCS between mammograms and cancer diagnosis. However, the non-cancerous breast was used for the analysis, which indicates the cancer abnormalities are not responsible for the association. Also, the V approach requires a consistent breast segmentation preprocessing stage, which is an easier task using FFDM in comparison with digitized film, and FFDM will be the screening modality most widely used. Finally, pixel dynamic range, digital resolution, and varying digital detector technologies may have an influence on V estimation; future research should evaluate this possibility.

The present disclosure references one or more publications. Each of the references in the present disclosure is incorporated herein by reference in its entirety. In addition, in the above, all measures and combinations of measures may include solely raw data or calibrated data, as well as a mixture of raw and calibrated measures.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. A method of assessing breast density for breast cancer risk applications, comprising:
   receiving digital image data including a plurality of pixels;
   calibrating the digital image data;
   measuring a variation of pixel values of the calibrated digital image data, wherein measuring a variation of pixel values of the calibrated digital image data further comprises at least one of calculating an $l^2$ norm or order derived therefrom or calculating an $l^1$ norm or order derived therefrom; and
   associating the variation of pixel values with a measure of risk for breast cancer, wherein the variation of pixel values correlates with at least one of a relative risk for breast cancer, an odds ratio for breast cancer, or an absolute risk prediction for breast cancer.

2. The method of claim 1, wherein measuring a variation of pixel values of the calibrated digital image data further comprises:
   calculating an $l^2$ norm or order derived therefrom;
   calculating an $l^1$ norm or order derived therefrom; and
   calculating a combination of measures based on results of the $l^2$ norm or order derived therefrom and the $l^2$ norm or order derived therefrom.

3. The method of claim 2, wherein calculating a combination of measures further comprises at least one of using a linear method, using a non-linear method, or using a Gram-Schmidt orthogonalization process, Principal Component Analysis, partial least squares or kernel-based method.

4. The method of claim 1, wherein calibrating the digital image data further comprises adjusting for image acquisition technique parameters by adjusting for at least one of variation in target/filter combination, x-ray tube voltage, radiation exposure, or compressed breast thickness.

5. The method of claim 4, wherein calibrating the digital image data is performed pixel-by-pixel.

6. The method of claim 4, wherein calibrating the digital image data further comprises:
   calculating an average pixel value of an n×n pixel region; and
   calibrating the average pixel value.

7. The method of claim 1, wherein the digital image data comprises an image having a breast tissue area and a background area, the method further comprising:
   segmenting the breast tissue area from the background area of the image.

8. The method of claim 7, further comprising:
   assigning pixel values within the breast tissue area a first value; and
   assigning pixel values within the background area a second value.

9. The method of claim 7, further comprising positioning a radial coordinate system origin at a side of the image at a first direction centroid position estimated from the segmented image.

10. The method of claim 9, further comprising eroding a percentage of the image between the radial coordinate system origin and a perimeter of the breast area along a radial direction.

11. A method of assessing breast density for breast cancer risk applications, comprising:
    receiving digital image data including a plurality of pixels;
    calibrating the digital image data;
    measuring a variation of pixel values of the calibrated digital image data, wherein measuring a variation of pixel values of the calibrated digital image data further comprises calculating the variation using an $n^{th}$ central or non-central moment of an integer or a fractional order or any real number order; and
    associating the variation of pixel values with a measure of risk for breast cancer, wherein the variation of pixel values correlates with at least one of a relative risk for breast cancer, an odds ratio for breast cancer, or an absolute risk prediction for breast cancer.

12. The method of claim 11, wherein measuring a variation of pixel values of the calibrated digital image data further comprises:
    calculating a first $n^{th}$ central or non-central moment;
    calculating a second $n^{th}$ central or non-central moment, the second $n^{th}$ central or non-central moment being different than the first $n^{th}$ central or non-central moment; and
    calculating a combination of measures based on results of the first and second $n^{th}$ central or non-central moments using at least one of a linear method or a non-linear method.

13. The method of claim 11, wherein calibrating the digital image data further comprises adjusting for image acquisition technique parameters by adjusting for at least one of variation in target/filter combination, x-ray tube voltage, radiation exposure, or compressed breast thickness.

14. A method of assessing breast density for breast cancer risk applications, comprising:
    receiving digital image data including a plurality of pixels;
    measuring a variation of pixel values of the digital image data, wherein measuring a variation of pixel values of the digital image data further comprises at least one of calculating an $l^2$ norm or order derived therefrom or calculating an $l^1$ norm or order derived therefrom: and
    associating the variation of pixel values with a measure of risk for breast cancer, wherein the variation of pixel values correlates with at least one of a relative risk for breast cancer, an odds ratio for breast cancer, or an absolute risk prediction for breast cancer.

15. The method of claim 14, wherein measuring a variation of pixel values of the digital image data further comprises:
    calculating an $l^2$ norm or order derived therefrom;
    calculating an $l^1$ norm or order derived therefrom; and calculating a combination of measures based on results of the $l^2$ norm or order derived therefrom and the $l^1$ norm or order derived therefrom.

16. The method of claim 15, wherein calculating a combination of measures further comprises at least one of using a linear method, using a non-linear method, or using a Gram-Schmidt orthogonalization process, Principal Component Analysis, partial least squares or kernel-based method.

17. The method of claim 14, wherein the digital image data comprises an image having a breast tissue area and a background area, the method further comprising:
    segmenting the breast tissue area from the background area of the image.

18. The method of claim 17, further comprising:
    assigning pixel values within the breast tissue area a first value; and
    assigning pixel values within the background area a second value.

19. A method of assessing breast density for breast cancer risk applications, comprising:
    receiving digital image data including a plurality of pixels;
    measuring a variation of pixel values of the digital image data, wherein measuring a variation of pixel values of the digital image data further comprises calculating the variation using an $n^{th}$ central or non-central moment of an integer or a fractional order or any real number order; and
    associating the variation of pixel values with a measure of risk for breast cancer, wherein the variation of pixel values correlates with at least one of a relative risk for breast cancer, an odds ratio for breast cancer, or an absolute risk prediction for breast cancer.

20. The method of claim 19, wherein calculating a variation of pixel values of the digital image data further comprises:
    calculating a first $n^{th}$ central or non-central moment;
    calculating a second $n^{th}$ central or non-central moment, the second $n^{th}$ central or non-central moment being different than the first $n^{th}$ central or non-central moment; and
    calculating a combination of measures based on results of the first and second $n^{th}$ central or non-central moments using at least one of a linear method and a non-linear method.

21. The method of claim 19, wherein the digital image data comprises an image having a breast tissue area and a background area, the method further comprising:
    segmenting the breast tissue area from the background area of the image.

* * * * *